US007993322B2

(12) United States Patent
Brud et al.

(10) Patent No.: US 7,993,322 B2
(45) Date of Patent: Aug. 9, 2011

(54) ABSORBENT GARMENT HAVING OUTER SHELL AND ADJUSTABLE ABSORBENT ASSEMBLY THEREIN

(75) Inventors: Lynn Brud, Middleton, WI (US); Michael Faulks, Neenah, WI (US); Emily Tran, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2017 days.

(21) Appl. No.: 10/737,101

(22) Filed: Dec. 15, 2003

(65) Prior Publication Data

US 2005/0131382 A1 Jun. 16, 2005

(51) Int. Cl.
*A61F 13/15* (2006.01)

(52) U.S. Cl. ........ 604/396; 604/393; 604/394; 604/395; 604/397; 604/398; 604/401; 604/402

(58) Field of Classification Search ............. 604/385.03, 604/385.14, 385.25–385.28, 386, 389–402; 2/400–408
See application file for complete search history.

(56) References Cited

U.S. PATENT DOCUMENTS

| | | |
|---|---|---|
| 1,664,298 A | 3/1928 | Katz |
| 1,971,558 A | 8/1934 | Goodman |
| 2,030,306 A | 2/1936 | Lain |
| 2,088,302 A | 1/1937 | McKeever |
| 2,252,019 A | 8/1941 | Meinecke et al. |
| 2,450,789 A | 10/1948 | Frieman |
| 2,566,325 A | 9/1951 | Ganz |
| 2,675,806 A | 4/1954 | Bram |
| 2,711,735 A | 1/1955 | Sabo |
| 2,838,047 A | 6/1958 | Sidnell |
| 2,842,129 A | 7/1958 | Ernstorff |
| 2,859,752 A | 11/1958 | Haber |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,648,699 A | 3/1972 | Anderson et al. |

(Continued)

FOREIGN PATENT DOCUMENTS

AT 168 478 6/1948

(Continued)

OTHER PUBLICATIONS

Paten Abstracts of Japan JP 2001-172,802 A: Description of Saito Akiko, "Method For Producing Disposable Trunks-Type Shorts," publication dated: Jun. 26, 2001.

(Continued)

*Primary Examiner* — Leslie R Deak
*Assistant Examiner* — Susan Su
(74) *Attorney, Agent, or Firm* — H. Michael Kubicki

(57) ABSTRACT

An absorbent garment having a garment-like outer shell and an absorbent assembly adapted for adjustable positioning therein is disclosed. In particular embodiments, the absorbent garment includes garment shell, at least one inner attachment member, and an absorbent assembly. The inner attachment member can be disposed at a waist region of the garment shell. The absorbent assembly can include a fastening component disposed at an end region, the first fastening component adapted for refastenable engagement to the inner attachment member. The inner attachment member can be configured such that a user may adjust a position of the refastenable engagement to the inner attachment member.

24 Claims, 12 Drawing Sheets

U.S. PATENT DOCUMENTS

| | | | |
|---|---|---|---|
| 3,678,516 A | | 7/1972 | Backer |
| 3,692,618 A | | 9/1972 | Dorschner et al. |
| 3,714,946 A | | 2/1973 | Rudes |
| 3,802,817 A | | 4/1974 | Matsuki et al. |
| 3,844,282 A | | 10/1974 | King |
| 3,849,241 A | | 11/1974 | Butin et al. |
| 3,859,667 A | | 1/1975 | Roy |
| 4,114,621 A | | 9/1978 | Mims, Jr. |
| 4,205,679 A | * | 6/1980 | Repke et al. .................. 604/366 |
| 4,231,358 A | * | 11/1980 | Atchison ......................... 602/58 |
| 4,244,368 A | | 1/1981 | Caradonna |
| 4,280,230 A | | 7/1981 | Lafleur |
| 4,310,929 A | | 1/1982 | Finlay |
| 4,338,939 A | | 7/1982 | Daville |
| 4,340,563 A | | 7/1982 | Appel et al. |
| 4,490,148 A | * | 12/1984 | Beckestrom ............ 604/385.26 |
| 4,555,245 A | | 11/1985 | Armbruster |
| 4,644,945 A | | 2/1987 | Thorner |
| 4,663,220 A | | 5/1987 | Wisneski et al. |
| 4,664,663 A | | 5/1987 | Brier |
| 4,671,793 A | | 6/1987 | Hults et al. |
| 4,704,116 A | | 11/1987 | Enloe |
| 4,745,636 A | | 5/1988 | Lunt |
| 4,870,958 A | | 10/1989 | Webster |
| 4,872,221 A | | 10/1989 | Stone, III |
| 4,892,598 A | | 1/1990 | Stevens et al. |
| 4,940,464 A | | 7/1990 | Van Gompel et al. |
| 4,955,880 A | | 9/1990 | Rodriquez |
| 4,964,860 A | * | 10/1990 | Gipson et al. .................. 604/391 |
| 4,965,122 A | | 10/1990 | Morman |
| 4,981,747 A | | 1/1991 | Morman |
| 5,046,272 A | | 9/1991 | Vogt et al. |
| 5,052,058 A | | 10/1991 | Mueller |
| 5,067,178 A | | 11/1991 | Katchka |
| 5,103,505 A | | 4/1992 | Llorens |
| 5,104,116 A | | 4/1992 | Pohjola |
| 5,135,522 A | | 8/1992 | Fahrenkrug et al. |
| 5,210,882 A | | 5/1993 | Moretz et al. |
| 5,212,839 A | * | 5/1993 | Sliman et al. ..................... 2/408 |
| 5,213,881 A | | 5/1993 | Timmons et al. |
| 5,217,782 A | | 6/1993 | Moretz et al. |
| 5,224,405 A | | 7/1993 | Pohjola |
| 5,226,992 A | | 7/1993 | Morman |
| D341,243 S | | 11/1993 | Costella et al. |
| 5,297,296 A | | 3/1994 | Moretz et al. |
| 5,303,424 A | | 4/1994 | Cromartie |
| 5,306,536 A | | 4/1994 | Moretz et al. |
| 5,315,716 A | | 5/1994 | Baum |
| 5,315,717 A | | 5/1994 | Moretz et al. |
| 5,336,545 A | | 8/1994 | Morman |
| 5,364,382 A | | 11/1994 | Latimer et al. |
| 5,370,634 A | | 12/1994 | Ando et al. |
| 5,379,462 A | | 1/1995 | Morgan et al. |
| 5,389,095 A | | 2/1995 | Suzuki et al. |
| 5,435,014 A | | 7/1995 | Moretz et al. |
| 5,445,628 A | | 8/1995 | Gipson et al. |
| 5,486,166 A | | 1/1996 | Bishop et al. |
| 5,490,846 A | | 2/1996 | Ellis et al. |
| 5,549,593 A | | 8/1996 | Ygge et al. |
| D377,557 S | | 1/1997 | Jagger |
| 5,649,913 A | | 7/1997 | Cohen |
| D382,386 S | | 8/1997 | Malone |
| 5,669,902 A | | 9/1997 | Sivilich |
| 5,690,626 A | | 11/1997 | Suzuki et al. |
| 5,690,627 A | | 11/1997 | Clear et al. |
| 5,700,256 A | | 12/1997 | Yamamoto et al. |
| 5,718,003 A | | 2/1998 | Gwinn |
| 5,766,389 A | | 6/1998 | Brandon et al. |
| 5,772,649 A | * | 6/1998 | Siudzinski .................... 604/386 |
| 5,790,983 A | | 8/1998 | Rosch et al. |
| 5,827,260 A | | 10/1998 | Suzuki et al. |
| 5,853,405 A | | 12/1998 | Suprise |
| 5,858,012 A | | 1/1999 | Yamaki et al. |
| 5,858,515 A | | 1/1999 | Stokes et al. |
| 5,876,394 A | | 3/1999 | Rosch et al. |
| 5,891,122 A | | 4/1999 | Coates |
| D408,964 S | | 5/1999 | Hernandez |
| 5,906,604 A | | 5/1999 | Ronnberg et al. |
| 5,953,754 A | | 9/1999 | Rosch et al. |
| 5,978,971 A | | 11/1999 | Wald |
| D417,940 S | | 12/1999 | Coates et al. |
| 6,009,558 A | | 1/2000 | Rosch et al. |
| 6,010,586 A | | 1/2000 | Suprise |
| 6,013,066 A | | 1/2000 | Samuelsson |
| 6,018,822 A | | 2/2000 | Hernandez |
| 6,098,557 A | | 8/2000 | Couillard et al. |
| 6,105,171 A | | 8/2000 | Niedermeyer |
| 6,108,823 A | | 8/2000 | Danes |
| 6,115,847 A | | 9/2000 | Rosch et al. |
| 6,142,983 A | | 11/2000 | Suprise et al. |
| 6,145,132 A | | 11/2000 | Towner |
| 6,149,637 A | | 11/2000 | Allen et al. |
| 6,168,585 B1 | | 1/2001 | Cesco-Cancian |
| 6,174,303 B1 | | 1/2001 | Suprise et al. |
| 6,192,521 B1 | | 2/2001 | Alberts et al. |
| 6,197,012 B1 | | 3/2001 | Mishima et al. |
| 6,293,934 B1 | | 9/2001 | Kumasaka |
| 6,293,936 B1 | | 9/2001 | Otsubo |
| 6,293,937 B2 | | 9/2001 | Matsushita et al. |
| 6,295,651 B1 | | 10/2001 | Kang |
| 6,312,420 B1 | | 11/2001 | Sasaki et al. |
| 6,342,050 B1 | | 1/2002 | Rönnberg et al. |
| 8,358,350 | | 3/2002 | Glaug at al. |
| 6,368,312 B1 | | 4/2002 | Otsubo |
| D456,995 S | | 5/2002 | Baker |
| 6,419,665 B1 | | 7/2002 | Cohen |
| 6,423,043 B1 | | 7/2002 | Gustafsson |
| 6,425,140 B1 | | 7/2002 | Vitches |
| 6,458,116 B1 | | 10/2002 | Matsushita |
| 6,475,201 B2 | | 11/2002 | Saito et al. |
| 6,475,205 B2 | | 11/2002 | Shimada et al. |
| 6,487,727 B1 | | 12/2002 | Harsant |
| 6,516,473 B2 | | 2/2003 | Saito |
| 6,539,554 B1 | | 4/2003 | Portela |
| 6,547,774 B2 | | 4/2003 | Ono et al. |
| 6,550,288 B2 | | 4/2003 | Browder, Jr. et al. |
| 6,558,364 B1 | | 5/2003 | Santa Cruz et al. |
| 6,585,840 B2 | | 7/2003 | Rabe et al. |
| 6,595,973 B2 | | 7/2003 | Sugito |
| 6,613,034 B2 | | 9/2003 | Nozaki et al. |
| 6,635,042 B2 | | 10/2003 | Kumasaka |
| 6,648,868 B2 | | 11/2003 | Sayama et al. |
| 6,651,463 B2 | | 11/2003 | Bonnin |
| 6,666,851 B2 | | 12/2003 | Otsubo et al. |
| 6,676,647 B2 | | 1/2004 | Shimada et al. |
| 6,761,712 B2 | | 7/2004 | Otsubo et al. |
| 2002/0004655 A1 | | 1/2002 | Shimada et al. |
| 2002/0035747 A1 | | 3/2002 | Kusibojoska et al. |
| 2002/0123732 A1 | | 9/2002 | Koyama et al. |
| 2002/0177825 A1 | | 11/2002 | Scovel |
| 2003/0023219 A1 | | 1/2003 | Nakaoka |
| 2003/0088955 A1 | | 5/2003 | Bridges |
| 2003/0114810 A1 | | 6/2003 | Weber |
| 2003/0115660 A1 | | 6/2003 | Hopkins |
| 2003/0216705 A1 | | 11/2003 | Coates |
| 2003/0217407 A1 | | 11/2003 | Andrews-Jones |
| 2003/0217803 A1 | | 11/2003 | Hermansson et al. |
| 2003/0229329 A1 | | 12/2003 | Mercier et al. |
| 2004/0060648 A1 | | 4/2004 | Thorson et al. |
| 2004/0082932 A1 | | 4/2004 | Lauritzen |
| 2004/0098791 A1 | | 5/2004 | Faulks |
| 2004/0102746 A1 | | 5/2004 | Mortell et al. |
| 2004/0107481 A1 | | 6/2004 | Mortell et al. |
| 2004/0108043 A1 | | 6/2004 | Otsubo |
| 2004/0116881 A1 | | 6/2004 | Nordness et al. |
| 2005/0125879 A1 | | 6/2005 | Yang et al. |
| 2005/0131377 A1 | | 6/2005 | Franke et al. |
| 2005/0131381 A1 | | 6/2005 | Kuen et al. |

FOREIGN PATENT DOCUMENTS

| | | |
|---|---|---|
| AU | 94/80371 B | 4/1995 |
| DE | 435 579 | 3/1925 |
| DE | 839 244 | 7/1949 |
| EP | 0 400 895 A1 | 12/1990 |
| EP | 0 217 032 B1 | 2/1992 |
| EP | 0 549 988 B1 | 6/1998 |
| EP | 0904758 A2 | 3/1999 |

| | | | |
|---|---|---|---|
| EP | 0911006 A1 | 4/1999 |
| EP | 1 048 231 A1 | 11/2000 |
| EP | 1 060 677 A1 | 12/2000 |
| EP | 1 092 355 A1 | 4/2001 |
| EP | 1 108 373 A1 | 6/2001 |
| EP | 1108371 A1 | 6/2001 |
| EP | 1108372 A1 | 6/2001 |
| EP | 1 125 571 A2 | 8/2001 |
| EP | 1159883 A1 | 12/2001 |
| EP | 1 166 730 A2 | 1/2002 |
| EP | 1179302 A2 | 2/2002 |
| EP | 1 188 427 A1 | 3/2002 |
| EP | 1184012 A1 | 3/2002 |
| EP | 0 763 353 B1 | 6/2002 |
| EP | 1219273 A2 | 7/2002 |
| EP | 1 247 506 A2 | 10/2002 |
| EP | 1 260 206 A2 | 11/2002 |
| EP | 0 933 072 B1 | 6/2003 |
| EP | 1 504 738 A2 | 2/2005 |
| FR | 1276791 | 10/1961 |
| GB | 701 081 A | 12/1953 |
| GB | 0774712 A | 5/1957 |
| GB | 774713 A | 5/1957 |
| GB | 1 342 022 A | 12/1973 |
| GB | 2 196 525 A | 5/1988 |
| GB | 2 208 263 A | 3/1989 |
| GB | 2 269 978 A | 3/1994 |
| GB | 2 269 998 A | 3/1994 |
| GB | 2 269 999 A | 3/1994 |
| GB | 2 327 859 A | 2/1999 |
| JP | 2000-355801 A | 12/2000 |
| JP | 2001-238909 A | 9/2001 |
| JP | 2001-248002 A | 9/2001 |
| JP | 2001-254202 A | 9/2001 |
| JP | 2001-309946 A | 11/2001 |
| JP | 2002-035022 A | 2/2002 |
| WO | WO 95/16421 A1 | 6/1995 |
| WO | WO 95/18589 A1 | 7/1995 |
| WO | WO 96/03949 A1 | 2/1996 |
| WO | WO 96/03950 A1 | 2/1996 |
| WO | WO 97/24091 A1 | 7/1997 |
| WO | WO 98/53785 A1 | 12/1998 |
| WO | WO 99/33421 A1 | 7/1999 |
| WO | WO 00/37009 A2 | 6/2000 |
| WO | WO 01/88245 A2 | 11/2001 |
| WO | WO 02/067833 A1 | 9/2002 |
| WO | WO 2004/073430 A2 | 9/2004 |

OTHER PUBLICATIONS

Patent Abstracts of Japan JP 2001-204,762 A: Description of Takahata Kenji, "Perfect Shorts Type Paper Diaper," publication date: Jul. 31, 2001.

US 5,915,536, 06/1999, Alberts et al. (withdrawn)

* cited by examiner

ABSORBENT GARMENT HAVING OUTER SHELL AND ADJUSTABLE ABSORBENT ASSEMBLY THEREIN

BACKGROUND OF THE INVENTION

This invention relates generally to absorbent garments, and more particularly to such absorbent garments having the appearance of conventional clothing and having a fit adjustment feature.

Personal wear garments and other articles find widespread use as personal care products including, without limitation, diapers, children's toilet training pants, disposable youth pants, adult incontinence garments, sanitary napkins and the like, as well as surgical bandages and sponges. The primary purpose of such articles is to take in and retain body exudates released by a wearer to thereby prevent soiling of the wearer's or caregiver's clothing. Certain absorbent articles are suitably disposable in that they are intended to be discarded after a limited period of use, i.e., the articles are not intended to be laundered or otherwise restored for reuse.

In particular absorbent articles such as children's training pants, various attempts have been made to make the pants more visually appealing, such as by applying certain graphics or other features which make the pants appear more like conventional clothing, and more particularly like conventional undergarments. Training pants represent an intermediate stage for a child between using diapers and using cloth underpants. By making the training pants more closely resemble the undergarments or other clothing that an older sibling or parent wears, it is believed that children ready for toilet training will be more amenable to wearing the training pants. In another example, some children require the use of nighttime disposable absorbent pants to address bed-wetting problems. Children requiring these absorbent pants generally desire the pants they are wearing to be as discreet as possible. Wearing an absorbent garment that resembles conventional clothing can be a significant benefit for such children.

One drawback to simply improving the external appearance of existing absorbent pants is that the entire pants must still be discarded after use. As a result, additional features which are added to entice children to wear the pants or otherwise conceal the absorbent look of the pants add further costs to making and using the pants. Moreover, clothes must still be worn over the absorbent pants, which can be uncomfortable and results in a rather bulky appearance. Also, to inhibit the leakage of exudates from absorbent articles such as training pants or other absorbent pants, it is important that the article fit generally snug against the wearer's body. For example, conventional training pants are constructed to provide a generally elastic fit about the wearer's waist and about the wearer's legs to inhibit leakage from the pants. However, many conventional garments that are worn about one's waist, such as certain styles of shorts, skirts, skorts, boxer shorts, swim trunks and the like, all have a more loose fitting appearance, particularly about the legs of the wearer. Moreover, because users of absorbent garments greatly vary in size and height, a means to more easily adjust the fit of conventional garments, particularly with respect to the rise of the garment and the positioning of the absorbent body against the wearer, is desired. Finally, it can in certain instances be useful to be able to remove and discard a soiled portion of a garment, but reuse a different portion of the garment.

Therefore a need exists for an absorbent garment that resembles conventional clothing, provides for an adjustable fit, and that in certain instances includes portions that are reusable.

SUMMARY OF THE INVENTION

In response to the aforementioned needs and deficiencies in the art, a new absorbent garment has been invented.

In one embodiment, the present invention pertains to an absorbent garment comprising a garment shell, first and second inner attachment members, and an absorbent assembly. The garment shell defines a longitudinal axis, a transverse axis, a first waist edge generally parallel to the transverse axis, a first waist region contiguous with the first waist edge, a second waist edge generally parallel to the transverse axis, and a second waist region contiguous with the second waist edge. The first inner attachment member is disposed at the first waist region, and the second inner attachment member is disposed at the second waist region, and each attachment member has a length dimension generally parallel to the longitudinal axis. The absorbent assembly is adapted for refastenable attachment to the garment shell, and the absorbent assembly has an inner surface adapted for contact with a wearer's body, an outer surface opposite the inner surface, a first end region in facing relationship with the first waist region of the garment shell, and a second end region in facing relationship with the second waist region of the garment shell. The absorbent assembly comprises a first fastening component disposed in the first end region, the first fastening component having a length dimension generally parallel to the longitudinal axis, and a second fastening component disposed in the second end region, the second fastening component having a length dimension generally parallel to the longitudinal axis. The first fastening component is adapted for refastenable engagement to the first inner attachment member, and the second fastening component is adapted for refastenable engagement to the second inner attachment member. The length dimension of the first inner attachment member is greater than the length dimension of the first fastening component.

In another embodiment, the present invention pertains to an absorbent garment comprising a garment shell, a first inner attachment member, and an absorbent assembly. The garment shell defines a longitudinal axis, a transverse axis, a first waist edge generally parallel to the transverse axis, a first waist region contiguous with the first waist edge, a second waist edge generally parallel to the transverse axis, and a second waist region contiguous with the second waist edge. The first inner attachment member is disposed at the first waist region and has a length dimension generally parallel to the longitudinal axis. The absorbent assembly is adapted for refastenable attachment to the garment shell, and the absorbent assembly has an inner surface adapted for contact with a wearer's body, an outer surface opposite the inner surface, a first end region in facing relationship with the first waist region of the garment shell, and a second end region in facing relationship with the second waist region of the garment shell. The absorbent assembly comprises a first fastening component disposed in the first end region, the first fastening component having a length dimension generally parallel to the longitudinal axis. The first fastening component is adapted for refastenable engagement to the first inner attachment member, and a portion of the absorbent assembly second end waist region is permanently attached to the garment shell second waist region. The length dimension of the first inner attachment member is greater than the length dimension of the first fastening component.

In yet another embodiment, the present invention pertains to an absorbent garment comprising a garment shell, a front inner attachment member, a back inner attachment member, and an absorbent assembly. The garment shell defines a longitudinal axis, a transverse axis, a front waist edge generally parallel to the transverse axis, a front waist region contiguous with the front waist edge, a back waist edge generally parallel to the transverse axis, and a back waist region contiguous with the back waist edge. The front inner attachment member is disposed at the front waist region, and the back inner attachment member is disposed at the back waist region, and each inner attachment member has a length dimension generally parallel to the longitudinal axis. The absorbent assembly is disposed within the garment shell, and the absorbent assembly has an inner surface adapted for contact with a wearer's body, an outer surface opposite the inner surface, a front end region in facing relationship with the front waist region of the garment shell, and a back end region in facing relationship with the back waist region of the garment shell. The absorbent assembly comprises a front fastening component at its front end region, the front fastening component having a length dimension generally parallel to the longitudinal axis, and a back fastening component at its back end region, the back fastening component having a length dimension generally parallel to the longitudinal axis. The front fastening component is refastenably engaged to the front inner attachment member. The front inner attachment member and the front fastening component both define continuously variable fastening surfaces.

In still another embodiment, the present invention pertains to a three-dimensional absorbent garment comprising a garment shell, a separately provided front inner attachment member, a back inner attachment member, and an absorbent assembly. The garment shell defines a longitudinal axis, a transverse axis, a front waist edge generally parallel to the transverse axis, a front waist region contiguous with the front waist edge, a back waist edge generally parallel to the transverse axis, and a back waist region contiguous with the back waist edge, the front and back waist regions being connected to one another to define a waist opening and at least one leg opening. The separately provided front inner attachment member is attached to the garment shell front waist region, and the front inner attachment member comprises an elastomeric, nonwoven material. The back inner attachment member is disposed at the back waist region. Each inner attachment member has a length dimension generally parallel to the longitudinal axis, and the front inner attachment member defines a longitudinal end flap portion unadhered to the garment shell for a distance of at least 75% of the length dimension of the front inner attachment member. The absorbent assembly is disposed within the garment shell, and the absorbent assembly has an inner surface adapted for contact with a wearer's body, an outer surface opposite the inner surface, a front end region in facing relationship with the front waist region of the garment shell, a back end region in facing relationship with the back waist region of the garment shell, and elasticized containment flaps. The absorbent assembly comprises a separately provided front fastening component attached to its front end region, the front fastening component having a length dimension generally parallel to the longitudinal axis, and a separately provided back fastening component attached to its back waist region, the back fastening component having a length dimension generally parallel to the longitudinal axis. The front fastening component is refastenably engaged directly to the front inner attachment member, and the back fastening component is refastenably engaged directly to the back inner attachment member. The length dimension of the front inner attachment member is at least three times the length dimension of the front fastening component, such that a user may adjust a position of refastenable engagement along the length dimension of the front inner attachment member.

Definitions

Within the context of this specification, each term or phrase below will include the following meaning or meanings.

"Attached" refers to the joining, adhering, connecting, bonding, or the like, of two or more elements, either directly or indirectly by way of an intervening element or elements.

"Disposed," "disposed on," "disposed with," "disposed at," "disposed near" and variations thereof are intended to mean that one element can be integral with another element, or that one element can be a separate structure bonded to or placed with or placed near another element.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Layer" when used in the singular can have the dual meaning of a single element or a plurality of elements.

"Liquid impermeable," when used in describing a layer or multi-layer laminate means that liquid body waste, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Longitudinal," and "transverse" or "lateral," have their customary meaning, as indicated by the longitudinal and transverse axes depicted in FIG. 4. The longitudinal axis lies in the plane of the article and is generally parallel to a vertical plane that bisects a standing wearer into left and right body halves when the article is worn. The transverse or lateral axis lies in the plane of the article generally perpendicular to the longitudinal axis.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

The term "microfibers" means small-diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881, entitled "A Nonwoven Web With Improved Barrier Properties".

"Non-woven" as used in reference to a material, web or fabric refers to such a material, web or fabric having a structure of individual fibers or threads that are interlaid, but not in a regular or identifiable manner as in a knitted fabric. Non-woven materials, fabrics or webs have been formed from many processes such as, for example, meltblowing processes, spunbonding processes, air laying processes, and bonded carded web processes. The basis weight of non-wovens is usually expressed in ounces of material per square yard (osy) or grams per square meter (gsm) and the fiber diameters are usually expressed in microns. (Note: to convert from osy to gsm, multiply osy by 33.91.).

"Operatively joined," with reference to the attachment of an elastic member to another element, means that the elastic member when attached to or connected to the element, or treated with heat or chemicals, by stretching, mechanical straining or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either direct, such as by joining the member directly to an element, or can be indirect, such as by means of another member disposed between the member and the element.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the article.

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al., each of which is incorporated by reference in its entirety and in a manner consistent with the present document. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

"Stretch bonded" refers to an elastic member being bonded to another member while the elastic member is extended at least about 25 percent of its relaxed length. More suitably, the term "stretch bonded" refers to the situation wherein the elastic member is extended at least about 100 percent, and even more suitably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Thermoplastic" describes a material which softens when exposed to heat and which substantially returns to a non-softened condition when cooled to room temperature.

These terms may be further defined with additional language in the remaining portions of the specification.

BRIEF DESCRIPTION OF THE DRAWINGS

Corresponding reference characters indicate corresponding parts throughout the drawings.

DETAILED DESCRIPTION

Figure 1:
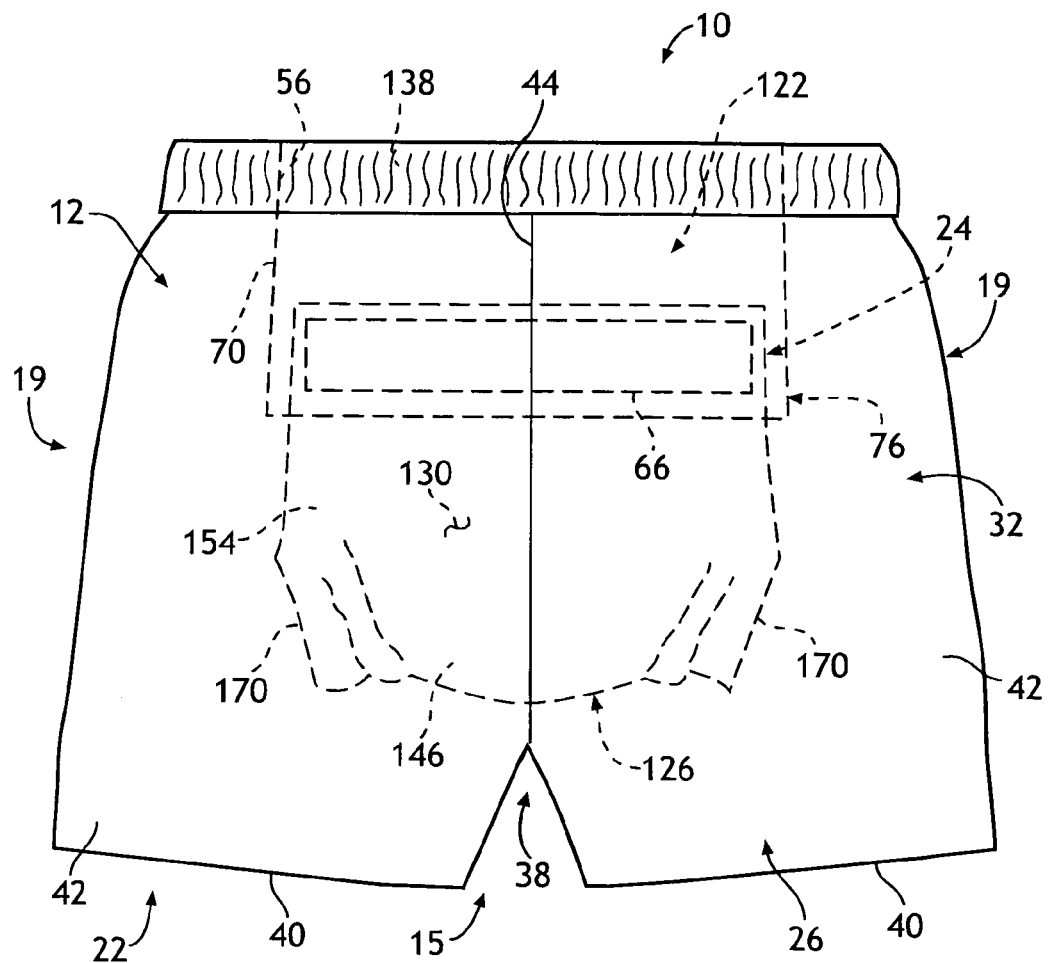
FIG. 1 is a front view of an absorbent garment according to one embodiment of the present invention.
Figure 2:
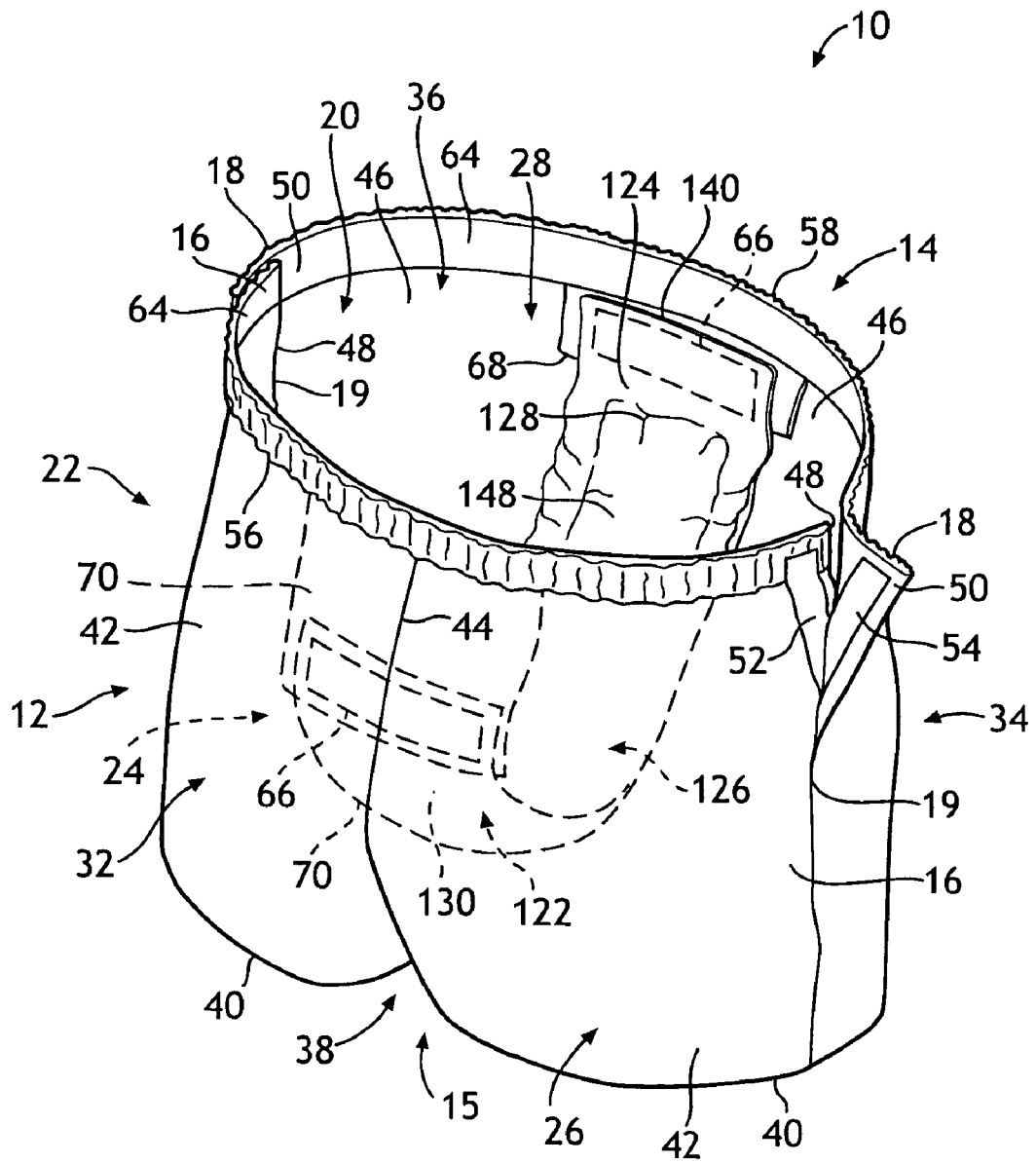
FIG. 2 is a perspective view of the absorbent garment of FIG. 1 with a side seam of the absorbent garment shown in a partially fastened, partially unfastened condition.

Referring now to the drawings, and in particular to FIGS. 1 and 2, an absorbent garment according to one embodiment of the present invention is indicated in its entirety by the reference numeral 10. The absorbent garment 10 is configured to be worn on a wearer's waist and generally has a front waist region, indicated generally at 12, a back waist region, indicated generally at 14 and a crotch region, indicated generally at 15. The front and back waist regions 12, 14 have respective side margins 16, 18 which are in particular embodiments attached to each other along side seams 19 of the garment to form a three-dimensional configuration of the garment during wear and having a waist opening, generally indicated at 20. As used herein, the term "seam" is intended to refer to a region along which two components are overlapped or otherwise in abutment with each other and may or may not be attached to each other.

As described further herein, the absorbent garment is suitably configured to resemble conventional clothing such as shorts (e.g., boxer shorts, gym shorts, running shorts, etc.), skirts, skorts (i.e., a combination of a skirt and a pair of shorts), swim trunks and the like, while providing the functions of conventional absorbent articles, such as taking in and retaining body exudates released by the wearer. The absorbent garment 10 comprises a garment shell, generally indicated at 22 and constructed to provide the desired resemblance of the garment to conventional clothing, and an absorbent assembly, generally indicated at 24, disposed within and releasably attached to the garment shell and constructed to take in and retain body exudates released by the wearer.

With particular reference to FIGS. 1 and 2, the garment shell 22 comprises a front panel assembly, which is generally indicated at 26, having laterally opposite side margins 48 and a back panel assembly, which is generally indicated at 28 in FIG. 2, having laterally opposite side margins 50. In the illustrated embodiment, the side margins 48 of the front panel assembly 26 broadly define the front side margins 16 of the absorbent garment 10 and the side margins 50 of the back panel assembly 28 broadly define the back side margins 18 of the absorbent garment. As will be described in further detail later herein, the side margins 48, 50 of the front and back panel assemblies 26, 28 of the garment shell 22 are overlapped and in particular embodiments are attached to each other to broadly define the side seams 19 of the absorbent garment 10, and to define the three-dimensional configuration of the garment shell during wear.

In its three-dimensional configuration as shown in FIGS. 1 and 2, the garment shell 22 has a front waist region 32 which at least in part defines the front waist region 12 of the absorbent garment 10, a back waist region 34 which at least in part defines the back waist region 14 of the absorbent garment, and front and back waist ends, designated 56 and 58, respectively, which together generally define a waist opening 36 of the garment shell. In the illustrated embodiment, the garment shell 22 is configured to resemble a pair of shorts and thus further has a crotch region 38 extending longitudinally between and interconnecting the front waist region 32 and the back waist region 34 of the garment shell. The crotch region 38 of the garment shell 22 at least in part defines the crotch region 15 of the absorbent garment 10, and also in part defines leg openings 40 of the garment shell (broadly referred to herein as outer leg openings of the absorbent garment). However, it is understood that the crotch region 38 of the garment shell 22 may be omitted (so that the crotch region 15 of the absorbent garment 10 is defined solely by the absorbent assembly 24 as described later herein), such as where the garment shell is intended to resemble a skirt (in which case only one leg opening 40 of the garment shell is provided to accommodate both legs of the wearer), without departing from the scope of this invention.

Figure 13:
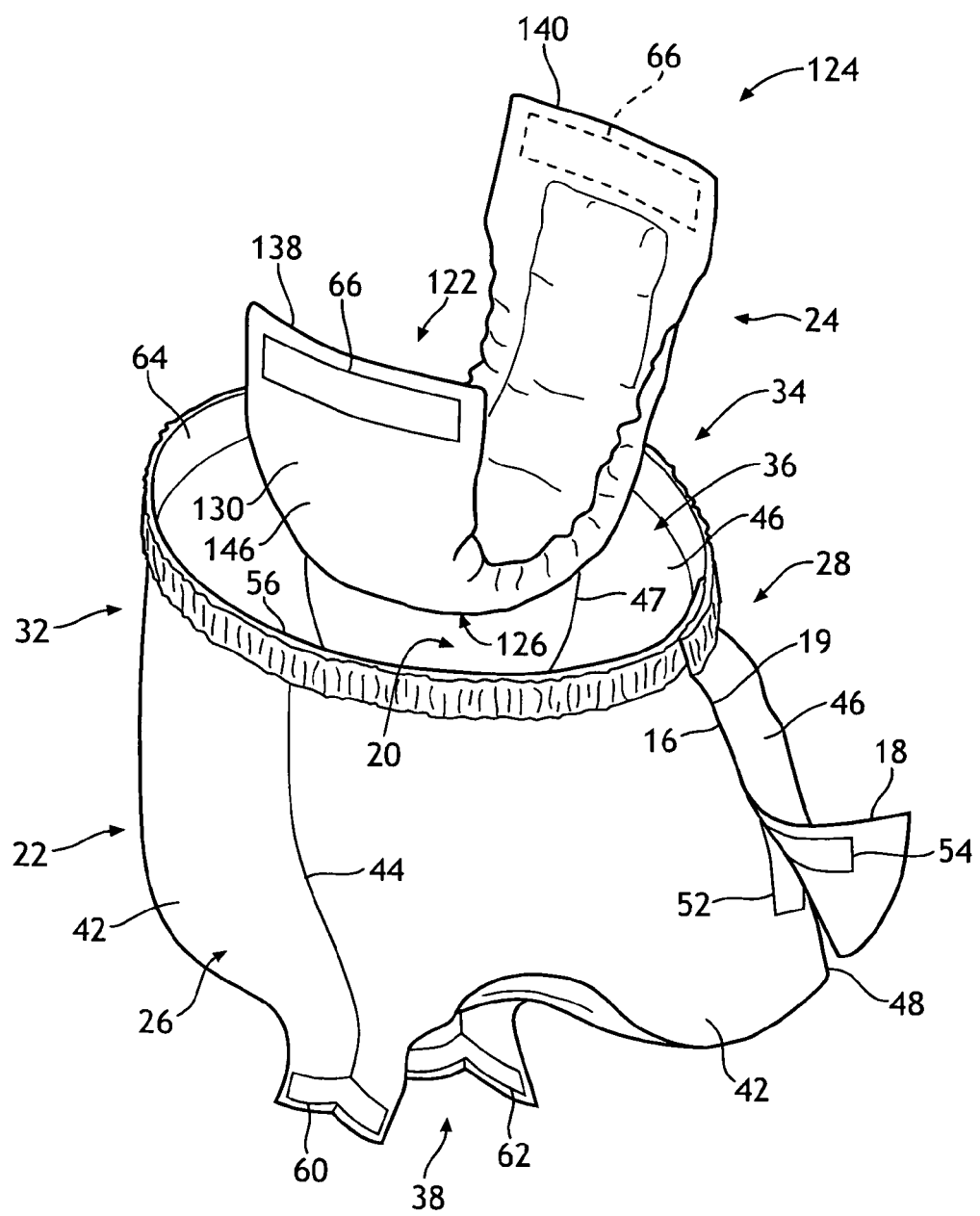
FIG. 13 is an exploded perspective view of another embodiment of the absorbent garment of the present invention.

The front panel assembly 26 of the garment shell 22 comprises a pair of panel members 42 which are in particular embodiments permanently attached to each other, such as by ultrasonic bonding, pressure bonding, thermal bonding, adhesive bonding, stitching or other conventional attachment technique, along a central seam 44 extending longitudinally from the front waist region 32 to the crotch region 38 of the garment shell. The back panel assembly 28 comprises a pair of panel members 46 configured and permanently attached to each other in a manner similar to the panel members 42 of the front panel assembly 26 along a central seam 47 (FIG. 13) extending longitudinally from the back waist region 34 to the crotch region 38 of the garment shell 22. It is understood, however, that each of the front and back panel assemblies 26, 28 may be constructed of a single panel member (e.g., of unitary construction) without departing from the scope of this invention. Alternatively, the front and back panel members 42, 46 on one side of the garment shell 22 may be formed integrally at the crotch region 38 thereof so that no attachment of the panel members is necessary at the leg openings.

The panel members 42, 46 of the front and back panel assemblies 26, 28 of the garment shell 22 can be constructed of any suitable material, and more suitably a material that provides a generally cloth-like texture. The panel members 42, 46 are, in particular embodiments, constructed of a material which is relatively durable so that the garment shell 22 can be re-used through multiple replacements of the absorbent assembly. It is also contemplated that the panel members 42, 46 can, but need not necessarily be, constructed of a material suitable for laundering to permit laundering of the garment shell. In yet another alternative, the garment shell is intended to be disposable after a single or several uses. As an example, the panel members 42, 46 may be constructed from natural and/or synthetic sources and may be constructed in any suitable manner including, but not limited, to nonwovens such as spunbond, meltblown, spunbond film laminates, bonded carded web, spunlace, hydroentangled, and needlepunched fabrics; knit fabrics such as stretch knit, fleece knit, herringbone knit, jersey knit, raschel knit; and woven fabrics such as broadcloth, twill, percale, poplin, muslin, cambric, chino, flannel, silks and woolens. The panel members 42, 46 are suitably liquid permeable, although it is understood that the panel members may be liquid impermeable without departing from the scope of this invention.

With particular reference to FIG. 2, the front and back panel assemblies 26, 28 of the garment shell 22 can be releasably attached to each other at the respective side margins 48, 50 of the panel assemblies. For example, in the illustrated embodiment a fastening component 52 is attached to each side margin 48 of the front panel assembly 26 and is adapted for refastenable engagement with a complementary fastening component 54 attached to each respective side margin 50 of the back panel assembly 28. Although the garment shell 22 as illustrated in FIG. 2 has the side margins 50 of the back panel assembly 28 overlapping the side margins 48 of the front panel assembly 26 upon releasable attachment, the garment shell can instead be configured so that the side margins of the front panel assembly overlap the side margins of the back panel assembly for releasable attachment.

The fastening components 52, 54 can comprise any refastenable fasteners suitable for garments, such as adhesive fasteners, cohesive fasteners, mechanical fasteners, or the like. In particularly suitable embodiments, the fastening components 52, 54 comprise mechanical fastening elements provided by interlocking geometric shaped materials such as hooks, loops, bulbs, mushrooms, arrowheads, balls on stems, male and female mating components, buckles, snaps, or the like. For example, in the illustrated embodiment the fastening components 52 comprise hook fasteners and the fastening components 54 comprise complementary loop fasteners arrayed so that the hook fasteners face generally away from the wearer. Alternatively, the fastening components 52 may comprise loop fasteners and the fastening components 54 may comprise complementary hook fasteners. One skilled in the art will recognize that the shape, density and polymer composition of the hooks and loops may be selected to obtain the desired level of engagement between the fastening components 52, 54. A more aggressive hook material may comprise a material with a greater average hook height and/or a greater percentage of directionally-aligned hooks. It is also contemplated that the fastening components 52, 54 can comprise interlocking similar surface fasteners, or adhesive and cohesive fastening elements such as an adhesive fastener and an adhesive-receptive landing zone or material; or the like.

Loop fastener as used herein refers to a fabric or material including a plurality of loop members. The loop material can be formed of any suitable material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in co-assigned U.S. Pat. No. 5,858,515 issued Jan. 12, 1999 to Stokes, et al., which is incorporated herein by reference.

The loop material may be attached to a base, or backing structure, and the composite then attached to the particular component of the absorbent garment 10, such as the front or back panel assemblies 26, 28 of the garment shell 22, or the loop material may be attached directly to the absorbent garment component so that the component (e.g., the garment shell) serves as a backing for the loop material, or the loop material may be formed integrally with the component (e.g., the garment shell), such as by constructing one or more layers or surfaces of the component to comprise a loop material.

Hook fastener as used herein refers to a fabric or material having a base or backing structure and a plurality of hook members extending upwardly from at least one surface of the backing structure. It should be understood that the term "hook" as used in reference to the hook members is non-limiting in the sense that the engaging elements of the hook fasteners may comprise shapes such as hooks, "T's", "mushrooms" or any other shape so long as they are adapted to releasably engage the loop fasteners so as to provide a secure, but non-destructive releasable attachment. It is understood that the attachment may be of limited lifetime, e.g., gradual degradation of the attachment may occur with repeated engagements and disengagements.

In contrast to the loop fasteners which suitably comprise a flexible fabric, the hook material may advantageously comprise a resilient material to minimize unintentional disengagement of the fastening components 52, 54 as a result of the hook material becoming deformed and catching on clothing or other items. The term "resilient" as used in reference to the hook fasteners refers to an interlocking material having a predetermined shape and the property of the interlocking material to resume the predetermined shape after being engaged and disengaged from a mating, complementary interlocking material.

Suitable hook material can be molded or extruded from nylon, polypropylene, polyethylene or another suitable material. Suitable single-sided hook materials for the fastening components 52, 54 as well as other fastening components described later herein are available from commercial vendors such as Velcro Industries B.V., Amsterdam, Netherlands or affiliates thereof, identified as Velcro HTH-829, which has a thickness of about 0.9 millimeters (35 mils) and HTH-851, which has a thickness of about 0.5 millimeters (20 mils); and Minnesota Mining & Manufacturing Co., St. Paul, Minn. U.S.A., including specific materials identified as CS-600. As with the loop fastener, it is understood that the hook material may be formed integrally with a component of the absorbent garment 10, such as the garment shell 22 in the instance of the fastening components 52, 54, without departing from the scope of this invention.

The fastening components 52, 54 are shown in FIG. 2 as having a generally rectangular shape, although they may instead be square, round, oval, curved or other suitable shapes. The fastening components 52, 54 extend along the respective side margins 48, 50 of the front and back panel assemblies 26, 28 generally from the waist ends 56, 58 of the panel assemblies to a position intermediate the waist ends and the leg openings 40 of the garment shell so that the absorbent garment side margins 16, 18 are releasably attached to each other along upper segments of the side seams 19. As an example, the fastening components 52, 54 suitably extend from the front and back waist ends 56, 58 of the garment shell 22 along the side margins 48, 50 thereof in the range of about 30 percent to about 90 percent of the length of the side margins (broadly, about 30 percent to about 90 percent of the length of the side seams 19 of the absorbent garment 10). However, it is understood that the fastening components 52, 54 may be longer or shorter without departing from the scope of this invention. Thus, in the illustrated embodiment, only a portion of the side seams 19 of the absorbent garment are releasably attached.

The segment of the garment shell 22 along which the side margins 48, 50 are not releasably attached (e.g., extending from the bottom of the fastening components 52, 54 to the leg openings 40 of the garment shell) are suitably free from any form of attachment. In such an embodiment, the non-refastenable portion of the side seams 19 of the absorbent garment 10 are referred to as being open and the side margins 16, 18 thereof are referred to as being unattached. Alternatively, the side margins 48, 50 of the front and back assemblies 26, 28 of the garment shell 22 may be non-refastenably (e.g., frangibly or permanently) attached to each other along the portion of side margins extending from the bottom of the fastening components to the leg openings 40, such as by adhesive, by thermal, ultrasonic, or pressure bonding, or by other suitable attachment techniques.

It is also contemplated that the fastening components 52, 54 may instead extend from the leg openings 40 of the garment shell partially up along the side margins 48, 50 of the front and back panel assemblies 26, 28 (e.g., so that only a lower segment of the side seams 19 of the absorbent garment are refastenable). The side margins 48, 50 extending from the tops of the fastening components 52, 54 to the waist ends 56, 58 of the garment shell 22 may be non-refastenably (e.g., frangibly or permanently) attached to each other in the manner described previously. In other embodiments, the fastening components 52, 54 may extend the entire length of the side margins 48, 50 of the front and back panel assemblies 26, 28 of the garment shell 22 (e.g., such that the side seams 19 of the absorbent garment 10 are refastenable along their full length). Also, while the fastening components 52, 54 are illustrated as being continuous along each respective side margin 48, 50, it is understood that two or more fastening components may be attached to each respective side margin in spaced relationship along the side margin without departing from the scope of this invention.

It is further contemplated that the side margins 48, 50 of the garment shell 22 may instead be permanently or frangibly (e.g., non-refastenably) attached along all or part of the full length thereof whereby no portions of the side margins are refastenable. It is also understood that the garment shell 22 may be formed to omit the side margins 48, 50 thereof, such as by integrally forming the respective front and back panel members 42, 46 on each side of the shell.

The amount of overlap between the side margins 48, 50 of the front and back panel assemblies 26, 28 at the side seams 19 of the garment shell 22 (broadly, the overlap of the side margins 16, 18 of the front and back waist regions 12, 14 of the absorbent garment 10) is suitably in the range of about 0.1 inches (2.5 millimeters (mm)) to about 6 inches (152.4 mm), and more suitably in the range of about 0.5 (12.7 mm) inches to about 3 inches (76.2 mm). It is contemplated that the fastening components 52, 54 on at least one of the front and back panel assemblies 26, 28 may have a width corresponding to the range of overlap to permit a variable fit of the absorbent garment over a relatively wide range of wearer sizes. It should be noted that the front and back panel assemblies 26, 28 can overlap at the side seams 19 in a "lap" seam manner as illustrated, or in a "butt" or "fin" seam manner (not shown).

The fastening components 52, 54 are suitably attached to the respective front and back panel assemblies 26, 28 by mechanical bonding. As used herein, mechanical bonding refers to non-adhesive bonding, such as by the application of pressure, ultrasonic energy, heat, laser energy or any other suitable form of energy which joins the fastening components to the panel assemblies 26, 28. Alternatively, or additionally, the fastening components 52, 54 may be adhered, such as by adhesive or cohesive means, to the respective front and back panel assemblies 26, 28. It is also contemplated that the fastening components 52, 54 may be formed integrally with the respective front and back panel assemblies 26, 28 and remain within the scope of this invention.

In addition to the front and back panel assemblies 26, 28 of the garment shell 22 being releasably attached to each other at the respective side margins 48, 50 thereof, or as an alternative thereto, it is contemplated that the panel assemblies may be releasably attached to each other at the crotch region 38 of the garment shell to allow the garment shell to be unfastened at the crotch region and pulled up relative to the absorbent assembly 24 for inspecting or otherwise replacing the absorbent assembly. For example, fastening components (not shown in FIG. 2 but indicated at 60, 62 in FIG. 13) may be attached to the front and back panel assemblies 26, 28 of the garment shell 22 generally at the crotch region 38 thereof to permit releasable attachment of the panel assemblies at the crotch region.

To further enhance the appearance of the absorbent garment 10 as well as the fit of the absorbent garment on the wearer's waist, one or more elastic members 64 (e.g., waistband elastics) can be operatively joined to the front and back panel assemblies 26, 28 generally at the respective waist ends 56, 58 thereof. For example, as best seen in FIG. 2, an elastic member 64 can be operatively joined to the front waist end 56 of the garment shell 22 on laterally opposite sides of the absorbent assembly 24. Another elastic member 64 can be operatively joined to the back waist end 58, also on laterally opposite sides of the absorbent assembly 24. The elastic members 64 can be operatively joined to the garment shell 22 while in a stretched condition so that upon retraction the elastic members gather the garment shell at the front and back waist ends 56, 58 to provide a gathered appearance and to further provide an elastic fit of the absorbent garment on the wearer's waist. Alternatively, it is contemplated that multiple elastic members (not shown) may be attached to each waist end 56, 58 of the garment shell 22 and extend laterally across all or only a portion of the width of the respective waist end without departing from the scope of this invention.

Figure 3:
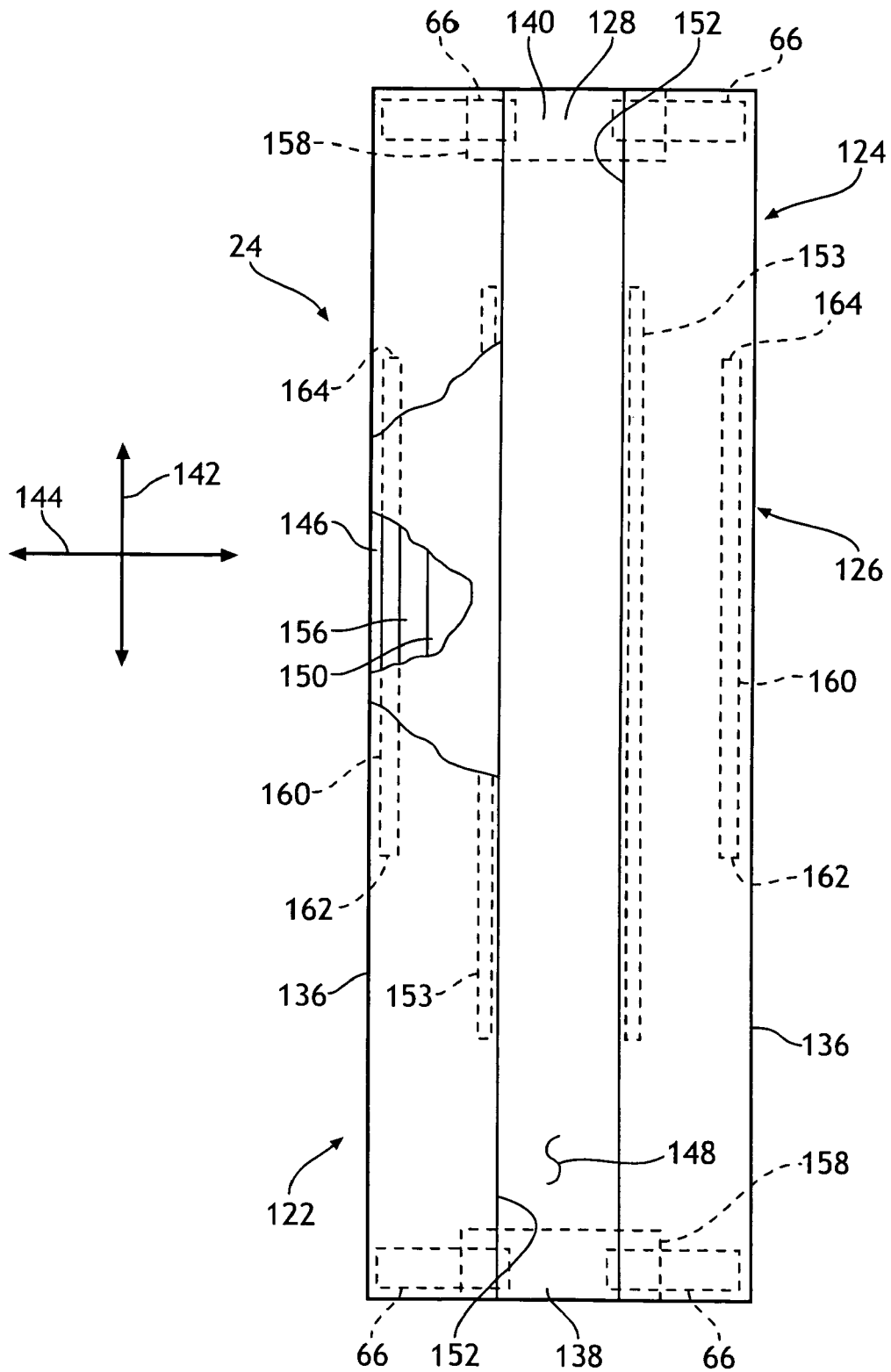
FIG. 3 is a plan view of an absorbent assembly of the absorbent garment of FIG. 1 with the absorbent assembly shown in an unfastened, stretched and laid flat condition, and showing the surface of the absorbent assembly that faces the wearer of the absorbent garment, and with portions cut away to show underlying features.
Figure 4:
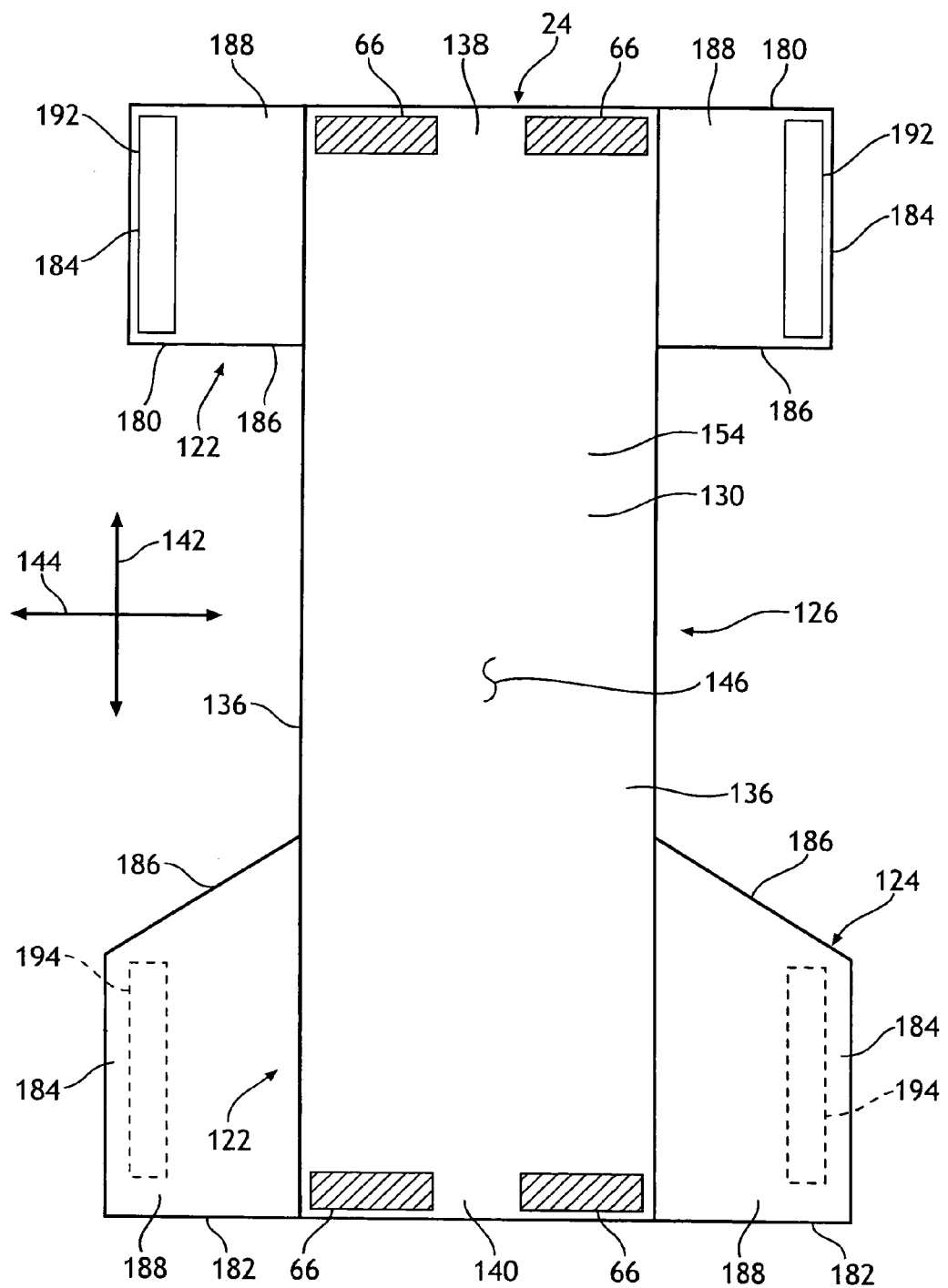
FIG. 4 is a plan view similar to FIG. 3a illustrating an alternative embodiment of an absorbent assembly.
Figure 5:
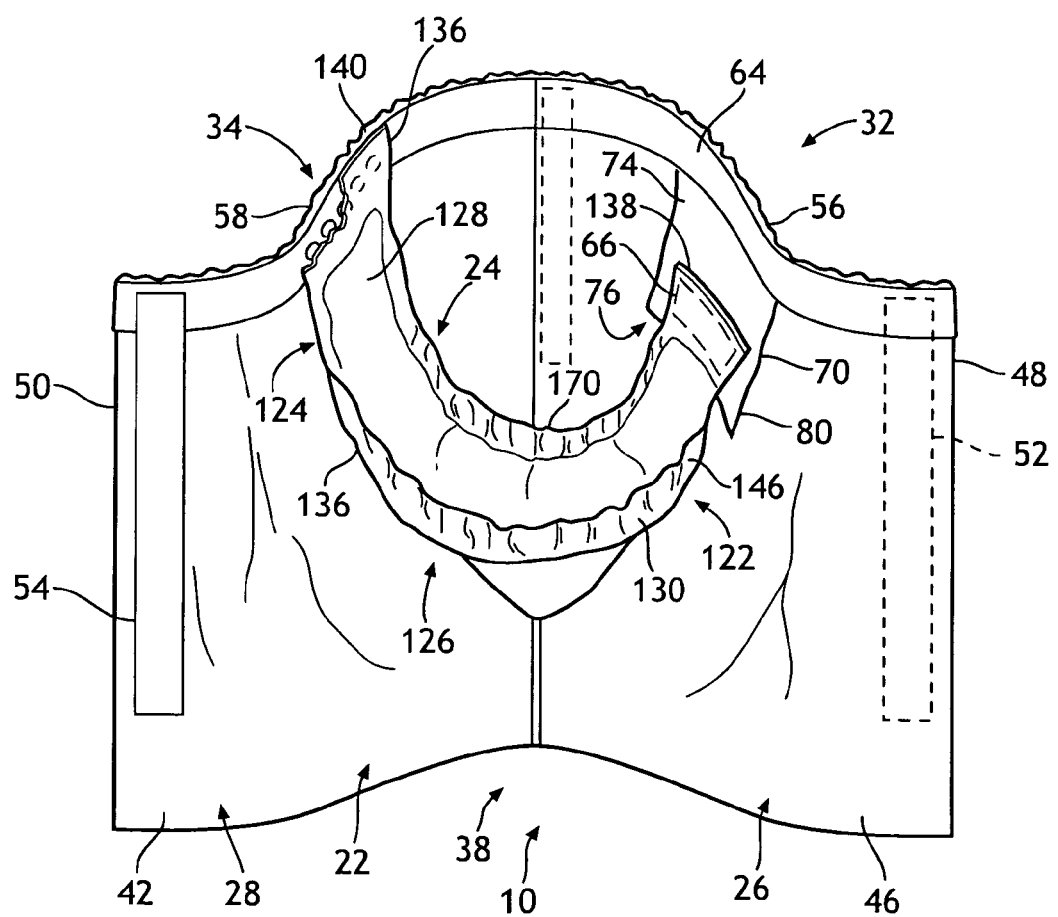
FIG. 5 is an elevated side view of one embodiment of the absorbent garment of the present invention, with a side seam of the absorbent garment shown in an unfastened condition.
Figure 6:
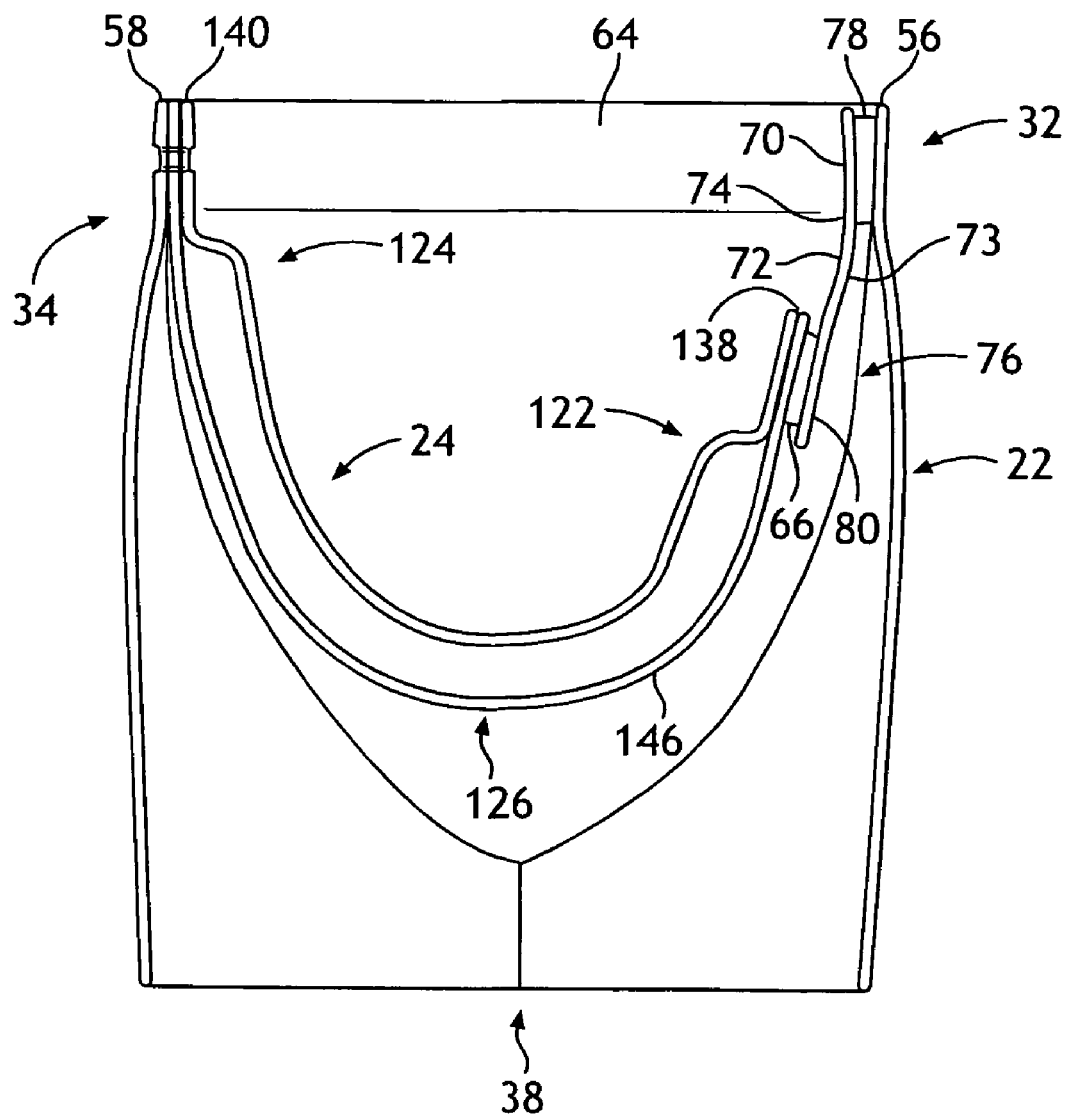
FIG. 6 is a side cross-sectional view of the absorbent garment of FIG. 5.
Figure 7:
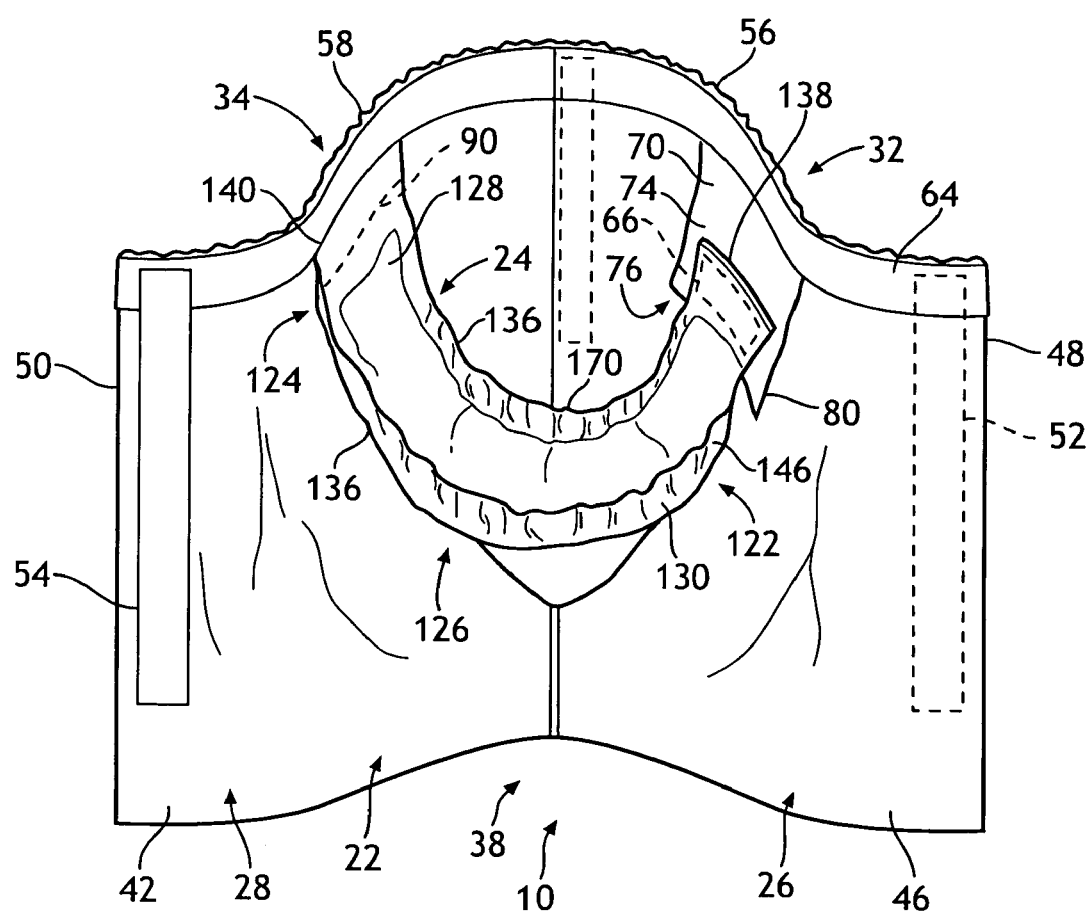
FIG. 7 is an elevated side view of another embodiment of the absorbent garment of the present invention, with a side seam of the absorbent garment shown in an unfastened condition.
Figure 8:
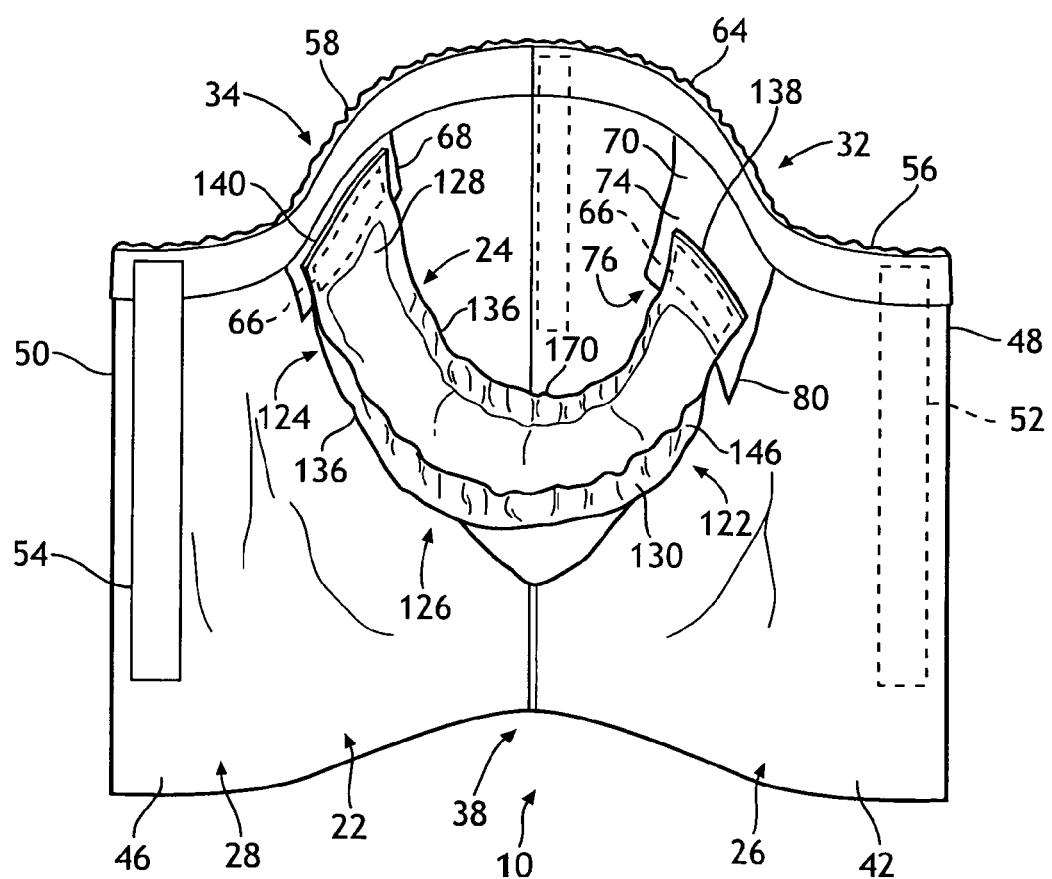
FIG. 8 is an elevated side view of another embodiment of the absorbent garment of the present invention, with a side seam of the absorbent garment shown in an unfastened condition.
Figure 9:
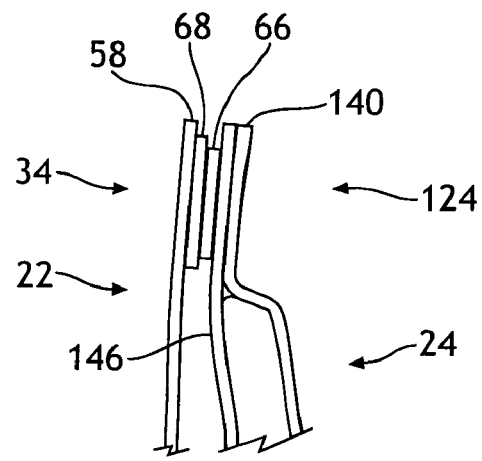
FIG. 9 is a side cross-sectional view of a waist region of the absorbent garment of FIG. 8.

With further reference to FIGS. 2-4, the absorbent assembly 24 comprises a front waist region 122, a back waist region 124, a crotch region 126 interconnecting the front and back waist regions, an inner surface 128 configured for contiguous relationship with the wearer, and an outer surface 130 opposite the inner surface. The front waist region 122 comprises the portion of the absorbent assembly which, when the absorbent garment 10 is worn, is positioned on the front of the wearer while the back waist region 124 comprises the portion of the absorbent assembly which is positioned on the back of the wearer. The crotch region 126 of the absorbent assembly 24 comprises the portion of the assembly which is positioned between the legs of the wearer and covers the lower torso of the wearer. With additional reference to FIG. 3, the absorbent assembly 24 also has laterally opposite side edges 136 and longitudinally opposite waist ends, respectively designated herein as front waist end 138 and back waist end 140.

The absorbent assembly 24 is suitably "disposable," which as used herein refers to articles that are intended to be discarded after a limited period of use instead of being laundered or otherwise restored for reuse. However, it is contemplated that the absorbent assembly may be re-useable and remain within the scope of this invention. By way of illustration only; various materials and methods for constructing the absorbent assembly 24 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 3A:
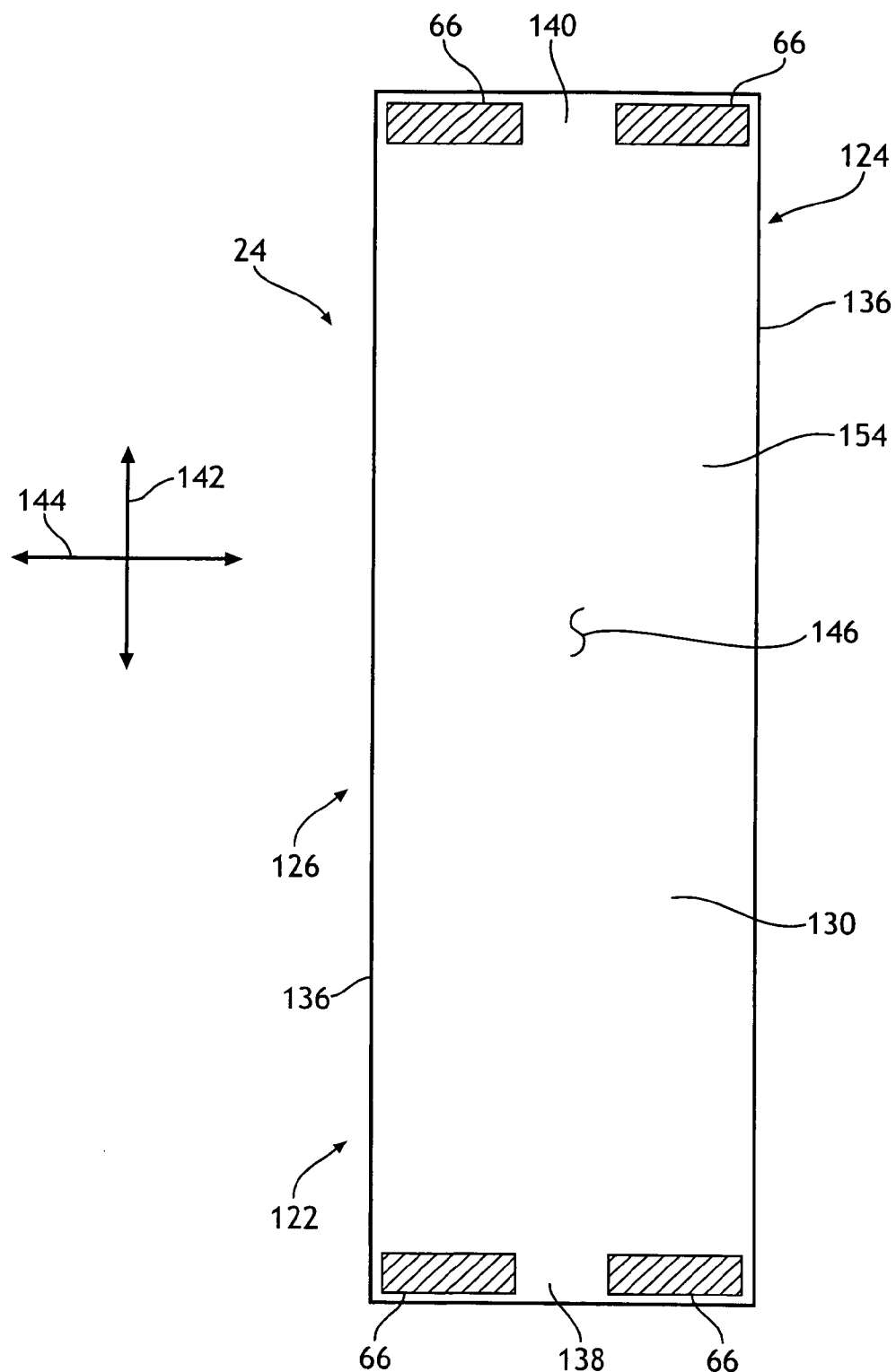
FIG. 3a is a plan view similar to FIG. 3, but showing the surface of the absorbent that faces away from the wearer of the absorbent garment.

Shown in FIGS. 3 and 3a is the absorbent assembly 24 detached from the garment shell 22 and in a laid-flat configuration. The absorbent assembly 24 is illustrated as being rectangular in shape, and has a longitudinal axis 142 and a transverse, or lateral axis 144. It is understood that the absorbent assembly 24 may be other than rectangular, such as hourglass-shaped, T-shaped, I-shaped or other suitable shape without departing from the scope of this invention. Referring to FIG. 3, the absorbent assembly 24 comprises an outer cover 146, a bodyside liner 148 in superposed relationship with the outer cover, an absorbent body 150 disposed between the outer cover and the bodyside liner, and a pair of laterally spaced containment flaps 152 configured to inhibit the transverse flow of body exudates on the liner to the side edges 136 of the absorbent assembly.

The outer cover 146 of the absorbent assembly 24 can, but need not, comprise a material which is substantially liquid impermeable, and can be stretchable or non-stretchable. As used herein, the term "stretchable" refers to a material that may be extensible or elastic. That is, the material may be extended, deformed or the like, without breaking, and may or may not significantly retract after removal of an extending force. As used herein, the term "elastic" refers to that property of a material where upon removal of an elongating force, the material is capable of recovering to substantially its unstretched size and shape, or the material exhibits a significant retractive force. The term "extensible" refers to that property of a material where upon removal of an elongating force, the material experiences a substantially permanent deformation, or the material does not exhibit a significant retractive force.

More suitably, the outer cover 146 comprises a multi-layered laminate structure in which at least one of the layers is liquid impermeable. For instance, referring to FIGS. 3 and 3A, the outer cover 146 can include a liquid permeable outer layer 154 and a liquid impermeable inner layer 156 which are suitably joined together by a laminate adhesive, ultrasonic bonds, pressure bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer 154 can be any suitable material and is desirably one that provides a generally cloth-like texture and appearance. One example of such a material is a 20 gsm (grams per square meter) spunbond polypropylene nonwoven web. The outer layer 154 may also be made of those materials described later herein from which the liquid permeable bodyside liner 148 is made.

The inner layer 156 of the outer cover 146 can be both liquid and vapor impermeable, or it may be liquid impermeable and vapor permeable. The inner layer 156 can be manufactured from a thin plastic film, although other flexible liquid impermeable materials may also be used. The liquid impermeable inner layer 156 prevents waste material from wetting articles, such as bed sheets and clothing, as well as the wearer and caregiver. A suitable liquid impermeable film for use as a liquid impermeable inner layer 156 of the outer cover 146 is a 0.02 millimeter polyethylene film commercially available from Pliant Corporation of Schaumburg, Ill., U.S.A.

Alternatively, the outer cover 146 may comprise a single layer of liquid impermeable material. As earlier mentioned, the liquid impermeable material can permit vapors to escape from the interior of the disposable absorbent article, while still preventing liquids from passing through the outer cover 146. For example, the outer cover 146 may be constructed of a microporous polymer film or a nonwoven fabric that has been coated or otherwise treated to impart a desired level of liquid impermeability. One such microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A. The single layer outer cover 146 may also be embossed and/or matte finished to provide a more cloth-like appearance.

The liquid permeable bodyside liner 148 is illustrated as overlying the outer cover 146 and absorbent body 150, and may but need not have the same dimensions as the outer cover 146. The bodyside liner 148 is desirably compliant, soft feeling, and non-irritating to the wearer's skin. Further, the bodyside liner 148 can be less hydrophilic than the absorbent body 150, to present a relatively dry surface to the wearer and to permit liquid to readily penetrate through the liner. Alternatively, the bodyside liner 148 can be more hydrophilic or can have essentially the same affinity for moisture as the absorbent body 150 to present a relatively wet surface to the wearer to increase the sensation of being wet. This wet sensation can be useful as a training aid. The hydrophilic/hydrophobic properties can be varied across the length, width and depth of the bodyside liner 148 and absorbent body 150 to achieve the desired wetness sensation or leakage performance.

The bodyside liner 148 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 148. For example, the bodyside liner 148 can be composed of a meltblown or spunbonded web of polyolefin fibers. The bodyside liner can also be a bonded-carded web composed of natural and/or synthetic fibers. The bodyside liner 148 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 148 or can be selectively applied to particular sections of the bodyside liner, such as the medial section along the longitudinal center line.

One example of a suitable liquid permeable bodyside liner 148 is a nonwoven bicomponent web having a basis weight of about 27 gsm. The nonwoven bicomponent web can be a spunbond bicomponent web, or a bonded carded bicomponent web. Suitable bicomponent fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent body 150 (FIG. 3) is positioned between the outer cover 146 and the bodyside liner 148, which can be joined together by any suitable means such as adhesives, ultrasonic bonds, pressure bonds, thermal bonds, or the like. The absorbent body 150 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent body 150 can suitably comprise a matrix of hydrophilic fibers, such as a web of cellulosic fluff, mixed with particles of a high-absorbency material commonly known as superabsorbent material. In a particular embodiment, the absorbent body 150 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent body 150 to better contain and absorb body exudates. The concentration of the superabsorbent particles can also vary through the thickness of the absorbent body 150. Alternatively, the absorbent body 150 can comprise a laminate of fibrous webs and superabsorbent material, a foam or other suitable web construction.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as BASF Corporation, Charlotte, N.C., U.S.A., and Stockhausen GmbH & Co. KG, D-47805 Krefeld, Federal Republic of Germany. Typically, a superabsorbent material is capable of absorbing at least about 10 times its weight in water, and suitably is capable of absorbing more than about 25 times its weight in water.

In one embodiment, the absorbent body 150 comprises a blend of wood pulp fluff and superabsorbent material. One suitable type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. In general, the superabsorbent material is present in the absorbent body 150 in an amount of from 0 to about 90 weight percent based on total weight of the absorbent assembly. The absorbent body 150 may or may not be wrapped or encompassed by a suitable wrap, such as a meltblown wrap or cellulosic tissue wrap, that aids in maintaining the integrity and/or shape of the absorbent assembly during use.

The containment flaps 152 are located generally adjacent to the side edges 136 of the absorbent assembly 24, and can extend longitudinally along the entire length of the absorbent assembly 24 as shown in FIG. 3 or only partially along the length of the absorbent assembly. Flap elastic members 153 (FIG. 3) can be operatively joined with the containment flaps 152 in a suitable manner as is well known in the art, such as by adhering the elastic members to the flaps while the elastic members are in a stretched condition so that the flaps are biased by the elastic members to a longitudinally gathered configuration. The elasticized containment flaps 152 can define a partially unattached distal edge (not shown), unattached to the liner 148, which assumes an upright configuration in at least the crotch region 126 of the absorbent assembly 24 during wear to form a seal (e.g., an elastic fit) against the wearer's body. Suitable constructions and arrangements for the containment flaps 152 are generally well known to those skilled in the art and are described in U.S. Pat. No. 4,704,116 issued Nov. 3, 1987 to Enloe, which is incorporated herein by reference. It is understood, however, that the containment flaps 152 may be omitted without departing from the scope of this invention.

To further enhance the fit of the absorbent garment 10 on the wearer and to further inhibit leakage of body exudates, the absorbent assembly can also have waist elastic members 158 (FIG. 3) and leg elastic members 160 (FIG. 3), as are known to those skilled in the art. The waist elastic members 158 can be operatively joined to the absorbent assembly 24 at the waist ends 138 and 140, such as by attaching the elastic members to the outer cover 146 and/or the bodyside liner 148 while the elastic members are in a stretched condition, so that upon retraction the elastic members gather the absorbent assembly at the waist ends to provide an elastic fit against the wearer's waist. In the illustrated embodiment the elastic members 158 which are operatively joined to the absorbent assembly 24, and the elastic members 64 which are operatively joined to the garment shell 22 on laterally opposite sides of the absorbent assembly, together provide an elastic fit of the absorbent garment 10 against substantially the entire waist of the wearer. The elastic members 158 are shown in FIG. 3 as extending only partially across the respective front and back waist ends 138, 140 of the absorbent assembly 24. It is understood, however, that the elastic members 158 may extend laterally across the full width of the absorbent assembly 24 at one or both waist ends 138, 140 without departing from the scope of this invention.

The leg elastic members 160 can be operatively joined to the outer cover 146 and/or the bodyside liner 148 and extend longitudinally adjacent the opposite side edges 136 generally through the crotch region 126 of the absorbent assembly 24. Each leg elastic member 160 has, in particular embodiments, a front terminal point 162 and a back terminal point 164, which represent the longitudinal ends of the elastic gathering caused by the leg elastic members.

The flap elastic members 153, the waist elastic members 158 (as well as the elastic members 64 operatively joined with the garment shell 22), and the leg elastic members 160 can be formed of any suitable elastic material. As is well known to those skilled in the art, examples of suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

The absorbent assembly 24 can also incorporate other materials or components designed primarily to receive, temporarily store, and/or transport liquid along the mutually facing surface with the absorbent body 150, thereby maximizing the absorbent capacity of the absorbent assembly. For example, one suitable additional component is commonly referred to as a surge layer (not shown). Surge layers are generally well known in the art as being constructed to quickly collect and temporarily hold liquid surges, and to transport the temporarily held liquid to the absorbent body 150.

Various woven and non-woven fabrics can be used to construct the surge layer. For example, the surge layer may be a layer made of a meltblown or spunbond web of synthetic fibers, such as polyolefin fibers. The surge layer may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge layer may be composed of a substantially hydrophobic material, and the hydrophobic material may optionally be treated with a surfactant or otherwise processed to impart a desired level of wettability and hydrophilicity.

Examples of materials suitable for the surge layer are set forth in U.S. Pat. No. 5,486,166 issued Jan. 23, 1996 in the name of C. Ellis et al.; U.S. Pat. No. 5,490,846 issued Feb. 13, 1996 in the name of Ellis et al.; and U.S. Pat. No. 5,364,382 issued Nov. 15, 1994 in the name of Latimer et al., the disclosures of which are hereby incorporated by reference in a manner consistent with the present document.

Referring to FIGS. 1-2 and 5-8, the absorbent assembly 24 is attached to the garment shell 22. The front and back waist regions 122, 124 of the absorbent assembly 24 are attached to the garment shell 22 generally at the front and back waist regions 32, 34 thereof, respectively. As described in more detail below, the absorbent 24 assembly may be permanently attached, removably attached, or refastenably attached to the garment shell 22. Further, the attachment may be directly to the garment shell 22, or indirectly by way of an intervening element or elements.

Referring to the exemplary embodiments shown in FIGS. 1-2 and 5-8, 10, and 12, the absorbent garment 10 of the present invention includes at least one inner attachment member 70 disposed at one or both of the garment shell waist regions 32 and 34. The absorbent assembly 24 is refastenably attached to the inner attachment member 70 to permit detachment, adjustment, and reattachment of the absorbent assembly. In this way, the position of the absorbent assembly 24 within the garment 10 can be adjusted to fit users of different sizes. Further, in certain embodiments as will be described shortly, the absorbent assembly 24 can be removed altogether from the absorbent garment 10, permitting it to be replaced, adjusted, or even omitted to allow the garment shell 22 to be worn without an absorbent assembly 24.

Referring to the exemplary embodiments shown in FIGS. 1, 2, 8 and 9, the front and back waist end 138, 140 of the absorbent assembly 24 are refastenably attached to the inner attachment member 70 and the garment shell back waist region 34, respectively. At least one fastening component 66 is attached to the outer cover 146 of the absorbent assembly 24 generally at the front waist end 138 thereof. An inner attachment member 70 is disposed at the inner surface of the front waist region 32 of the garment shell 22 for refastenable attachment to the fastening components 66 at the front waist end 138 of the absorbent assembly 24. One or more additional fastening components 66 can be attached to the outer cover 146 of the absorbent assembly 24 generally at the back waist end 140 thereof with corresponding fastening components 68 (FIGS. 8 and 9) being attached to the inner surface of the back waist end 58 of the garment shell 22 for releasable attachment to the fastening components 66 at the back waist end 140 of the absorbent assembly 24.

The fastening components 66, 68 can comprise any refastenable fasteners suitable for garments as described previously herein, such as adhesive fasteners, cohesive fasteners, mechanical fasteners, or the like. In particularly suitable embodiments, the fastening components 66, 68 comprise mechanical fastening elements provided by interlocking geometric shaped materials such as hooks, loops, bulbs, mushrooms, arrowheads, balls on stems, male and female mating components, buckles, snaps, or the like. For example, in the illustrated embodiment, the fastening components 66 attached to the front and back waist ends 138, 140 of the absorbent assembly 24 comprise hook fasteners, and the inner attachment member 70, and the fastening components 68 (FIGS. 8 and 9) attached to the back waist end 58 of the garment shell 22 comprise complementary loop fasteners.

Alternatively, the fastening components 66 may comprise loop fasteners, and the inner attachment member 70 and the fastening components 68 (FIGS. 8 and 9) may comprise complementary hook fasteners. In another embodiment, the fastening components 66, 68 can comprise interlocking similar surface fasteners, or adhesive or cohesive fastening elements such as an adhesive fastener and an adhesive-receptive landing zone or material, or the like. One skilled in the art will recognize that the shape, density and polymer composition of the hooks and loops may be selected to obtain the desired level of engagement between the fastening components 66, 68. A more aggressive hook material may comprise a material with a greater average hook height and/or a greater percentage of directionally-aligned hooks.

The fastening components 66, 68 are illustrated as being rectangular in shape, although it is understood that the fastening components may be square, circular, curved or other suitable shape. The fastening components 66, 68 suitably each have a length (e.g., determined parallel to the longitudinal axis of the garment 10 in the illustrated embodiment) in the range of about 6 mm to about 38, and a width (e.g., determined parallel to the transverse axis of the garment 10 in the illustrated embodiment) no greater than the width of the absorbent assembly 24. However, it is contemplated that the fastening components 66, 68 may be larger or smaller in width and/or length without departing from the scope of this invention. In certain embodiments, such as those shown in FIGS. 1, 2, 5, 7, 8, and 13, a single fastening component 66 can be attached to the absorbent assembly 24 at one or both of the respective front and back waist ends 138, 140. In such an embodiment, the single fastening component(s) 66 can suitably be laterally positioned centrally on the absorbent assembly 24 at one or both of the respective waist ends 138, 140 thereof and may extend partially or fully across the full width of the absorbent assembly at the waist ends. In other embodiments, such as those representatively illustrated in FIGS. 3, 3a, and 4, two or more fastening components 66 may be positioned at one or both waist ends 138, 140 of the absorbent assembly 24 in a laterally spaced manner.

The fastening components 66 of the illustrated embodiment may be attached to the front and back waist ends 138, 140 of the absorbent assembly 24 by adhesive, by thermal bonding or ultrasonic bonding, or by any other suitable attachment technique. The fastening component or components 68 may be attached to the back waist end 58 of the garment shell 22 by any of these attachment techniques as well, and may be attached using the same attachment technique used to attach the fastening components 66 to the front and back waist ends 138, 140 of the absorbent assembly 24, or by a different attachment technique. It is also contemplated that the fastening components 66 may be attached to the front and back waist ends 138, 140 of the absorbent assembly 24 by being formed integrally therewith. Likewise, the fastening component 68 may be formed integrally with the back waist end 58 of the garment shell 22.

With the absorbent assembly 24 refastenably attached to the garment shell 22, the elasticized side edges 136 of the absorbent assembly 24 generally define laterally opposite elastic leg openings 170 (FIGS. 1, 5, 7, 8, and 12)of the absorbent assembly (broadly, inner leg openings of the absorbent garment 10) whereat the absorbent assembly 24 provides an elastic fit against at least part of the wearer's legs. The leg openings 40 of the garment shell 22 broadly define outer leg openings of the absorbent garment 10, separate (e.g., discrete) from the absorbent assembly leg openings 170, whereat the absorbent garment hangs generally loose about the wearer's legs.

In an alternative embodiment of the absorbent assembly 24 as shown in FIG. 4 (as well as in another alternative embodiment of an absorbent garment 10 shown in FIG. 12 and described further below), the absorbent assembly 24 may be a brief-style absorbent assembly such as children's training pants, swim pants or child or adult enuresis or incontinence products which are configured for wearing about the full waist of the wearer. More particularly, in addition to the components illustrated in FIG. 3 and described previously herein, the absorbent assembly 24 illustrated in FIGS. 4 and 12 further comprises front and back side panels, designated 180 and 182, respectively, disposed generally on each side of the absorbent assembly 24 at the respective front and back waist regions 122, 124 of the absorbent assembly and extending transversely outward therefrom. The side panels 180, 182 may be attached to the bodyside liner 148 and/or to the outer cover 146 of the absorbent assembly 24 by adhesive, or by thermal or ultrasonic bonding, or by other suitable attachment techniques known to those skilled in the art. Alternatively, the side panels 180, 182 can be formed as an integral portion of a component of the absorbent assembly 24. For example, the side panels 180, 182 can comprise a generally wider portion of the outer cover 146, the bodyside liner 148, and/or another component of the absorbent assembly 24.

The front and back side panels 180, 182 have respective outer edges 184 which broadly define the side edges of the absorbent assembly 24 at the front and back waist regions 122, 124 thereof. The side panels 180, 182 also have respective leg end edges 186 disposed toward the longitudinal center of the absorbent assembly 24, and respective waist end edges 188 which further define the respective front or back waist end 138, 140 of the absorbent assembly 24. The leg end edges 186 of the back side panels 182 can be curved and/or angled (FIG. 4) relative to the transverse axis 144 to provide a better fit of the absorbent assembly 24 about the wearer's legs. However, it is understood that the leg end edges 186 of the front side panels 180 may additionally, or alternatively, be curved or angled, or none of the leg end edges may be curved or angled, without departing from the scope of this invention.

The side panels 180, 182 suitably comprise a stretchable material, and more suitably an elastic material, capable of stretching in a direction generally parallel to the transverse axis 144 of the absorbent assembly 24. Suitable elastic materials, as well as one process of incorporating elastic side panels into brief-style absorbent assemblies, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may comprise other woven or nonwoven materials, such as those described above as being suitable for the outer cover 146 or bodyside liner 148; mechanically pre-strained composites; stretchable but inelastic (e.g., extensible) materials; or non-stretchable materials.

Figure 12:
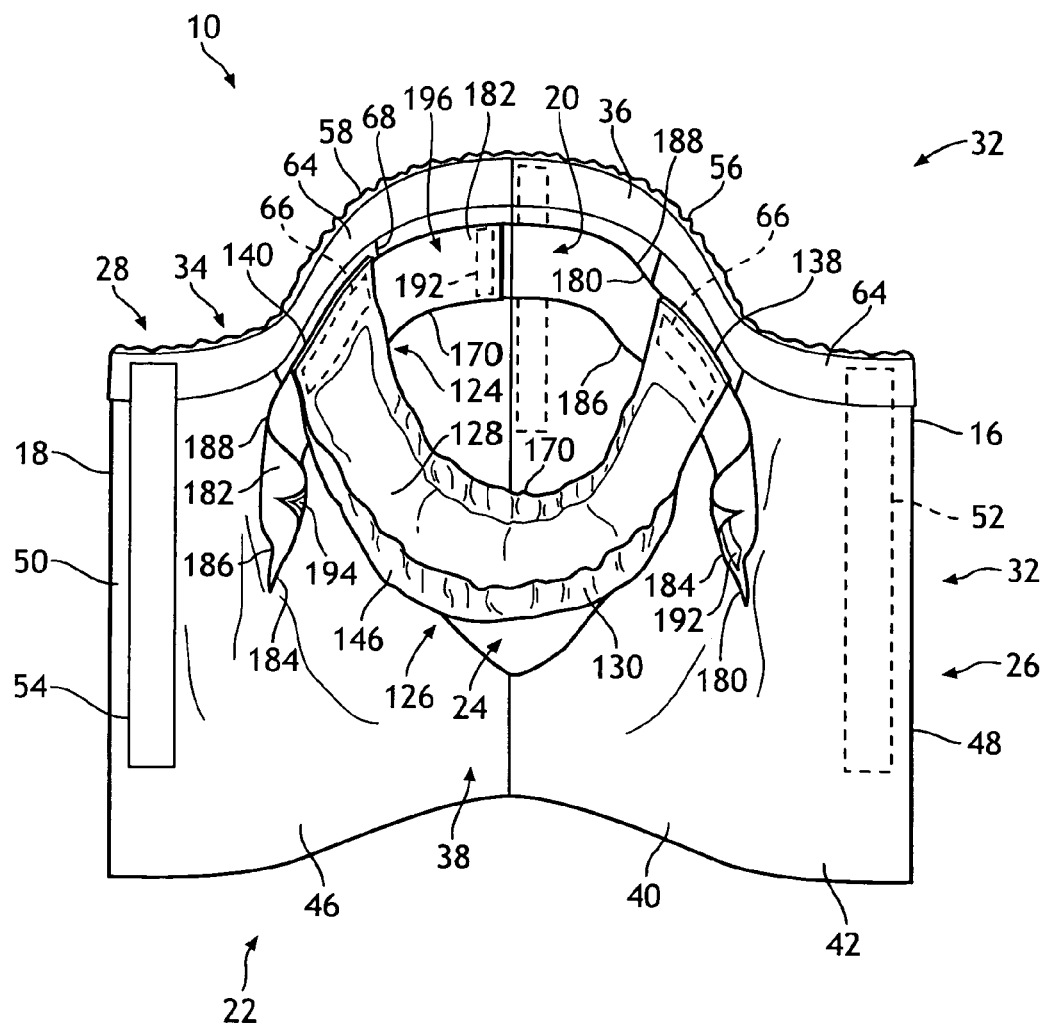
FIG. 12 is an elevated side view of another embodiment of an absorbent garment incorporating an absorbent assembly similar to the one shown in FIG. 4, with a side seam of the absorbent garment shown in an unfastened condition and one pair of side panels of the absorbent assembly also shown in an unfastened condition.

Still referring to FIGS. 4 and 12, the absorbent assembly 24 of this embodiment further comprises laterally spaced first fastening components 192 attached to the front side panels 180 generally at the outer edges 184 thereof and complementary second fastening components 194 attached to the back side panels 182 generally at the outer edges thereof and adapted for refastenable engagement with the first fastening components to releasably attach the side panels together to thereby define a three-dimensional configuration of the absorbent assembly that can be worn about the waist of the wearer. The fastening components 192, 194 can comprise any of the refastenable fasteners previously described herein as being suitable for absorbent garments, such as adhesive fasteners, cohesive fasteners, mechanical fasteners, or the like. In particular embodiments the fastening components 192, 194 comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 192 comprise hook fasteners and the second fastening components 194 comprise complementary loop fasteners. Alternatively, the first fastening components 192 may comprise loop fasteners and the second fastening components 194 may comprise complementary hook fasteners. In another embodiment, the fastening components 192, 194 can comprise interlocking similar surface fasteners, or adhesive or cohesive fastening elements such as an adhesive fastener and an adhesive-receptive landing zone or material; or the like. One or more of the fastening components 192 and 194 can be separate from and attached to the side panels 180 and 182, or can be integrally formed therewith. It is also contemplated that the side panels 180, 182 of the absorbent assembly may instead be non-refastenably (e.g., permanently or frangibly) attached together, such as by adhesive, by thermal bonding, pressure bonding, ultrasonic bonding, stitching, or by other suitable attachment techniques and remain within the scope of this invention.

In the illustrated embodiment, the back side panels 182 overlap the front side panels 180 upon releasable attachment of the side panels. However, it is understood that the front side panels 180 may instead overlap the back side panels 182 without departing from the scope of this invention. The side panels 180, 182 are otherwise unattached to the garment shell 22 so that upon assembling the absorbent garment 10, the side panels are attached to each other and then the side margins 48, 50 of the front and back panel assemblies 26, 28 of the garment shell 22 are separately attached to each other.

In the embodiment representatively illustrated in FIG. 12, the side panels 180, 180, when attached to each other to define the three-dimensional configuration of the absorbent assembly 24, define, together with the front and back waist ends 138, 140 of the absorbent assembly, a waist opening 196 of the absorbent assembly separate from the waist opening 36 of the garment shell 22. The side edges 136 of the absorbent assembly 24, including the leg end edges 186 of the side panels 180, 182, define the elastic leg openings 170 (broadly, the inner leg openings of the absorbent garment 10) of the absorbent assembly 24 about which the absorbent assembly provides an elastic fit against the wearer's leg. The attached side margins 48, 50 of the front and back panel assemblies 26, 28 of the garment shell 22 broadly define the side margins 16, 18 of the absorbent garment 10 which are, in particular embodiments, releasably attached along all or part of the side seams 19 of the absorbent garment. As in the embodiment of FIG. 2, the leg openings 40 of the garment shell 22 shown in FIG. 12 (when the garment shell is in its fully fastened configuration) broadly define outer leg openings of the absorbent garment 10 separate (e.g., discrete) from the leg openings 170 of the absorbent assembly whereat the absorbent garment hangs generally loose about the wearer's legs.

As representatively illustrated in FIGS. 1-2 and 5-8, an inner attachment member 70 is disposed at the garment shell front waist region 32. The inner attachment member 70 defines a fastening surface 74 refastenably engageable with the fastening components 66 present on the absorbent assembly 24. For example, the absorbent assembly 24 can be refastenably attached to the inner attachment member 70 by fastening components 66 attached to the outer surface of front and back waist ends 138, 140 of the absorbent. In the illustrated embodiment, the fastening components 66 attached to the front and back waist ends 138, 140 of the absorbent assembly 24 are hook fasteners. In such an embodiment, the inner attachment member 70 includes a suitable loop material for releasable attachment to the hook fasteners 66 of the absorbent assembly 24.

The inner attachment member can define a fastening surface 74 suitable for engagement with fasteners 66 over its entire surface, or over only a portion of its surface. For example, if fasteners 66 are hook-type fasteners, the inner attachment member 70 may integrally comprise a material which functions as a complementary, loop-type engaging surface. In an alternative embodiment (not shown), the inner attachment member 70 may include one or more complementary mating fastening components bonded to the inner attachment member 70 for refastenable attachment to the fastening component 66 attached to the front waist end 138 of the absorbent assembly 24. In such an embodiment, the fastening components attached to the inner attachment member 70 and to the absorbent assembly 24 may comprise any of the fastening components previously described herein as being suitable for absorbent garments. In particular embodiments, the entire fastening surface 74 of the inner attachment member 70 is a variable-location fastening surface, such that the fastening component 66 can be releaseably positioned anywhere along the entire length of the inner attachment member 70.

In particular embodiments, the inner attachment member 70 is permanently attached to the garment shell 22, such as by adhesive, by thermal, pressure, or ultrasonic bonding, or by other suitable attachment technique. For example, the inner attachment member can be attached by an adhesive 78, as representatively illustrated in FIGS. 6 and 10. Alternatively, the inner attachment member 70 can be releasably attached to the garment shell 22, such as by fastening components attached to the inner surface of the garment shell generally at the front waist end 56 thereof (not shown). For example, hook fasteners can be attached to the inner surface of the garment shell 22, and the inner attachment member 70 can provide a suitable loop material for releasable attachment to the hook fasteners. Alternatively, the inner attachment member 70 may have one or more fastening components (not shown) attached thereto for releasable attachment to fastening components (not shown) attached to the front waist end 56 of the garment shell 22. In yet another embodiment, representatively illustrated in FIG. 11, the inner attachment member 70 may be formed integrally with the garment shell 22, such that the inner attachment member 70 defines at least part of the inner surface 27 of the front panel assembly 26 of the garment shell 22, and such that the at least part of the inner surface 27 of the garment shell 22 defines the fastening surface 74.

The inner attachment member 70 has a length dimension generally parallel to the longitudinal axis 142. In particular embodiments, at least a portion of the inner attachment member 70 is not adhered to the garment shell 22, so as to define an unadhered flap portion 80. For example, as can be seen in the embodiment shown in FIGS. 5-8, the inner attachment member 70 can be only partially attached to the garment shell 22, and can include a flap portion 80 unadhered to the garment shell 22 at a longitudinal end region 76 of the inner attachment member 70. In particular embodiments, the unadhered end flap portion 80 comprises at least about 50% of the length dimension of the inner attachment member 70, and more particularly at least about 75% of the length dimension of the inner attachment member 70. Furthermore, in certain embodiments, the fastening component 66 on the absorbent assembly 24 is refastenably engaged to the end flap portion 80.

Figure 10:
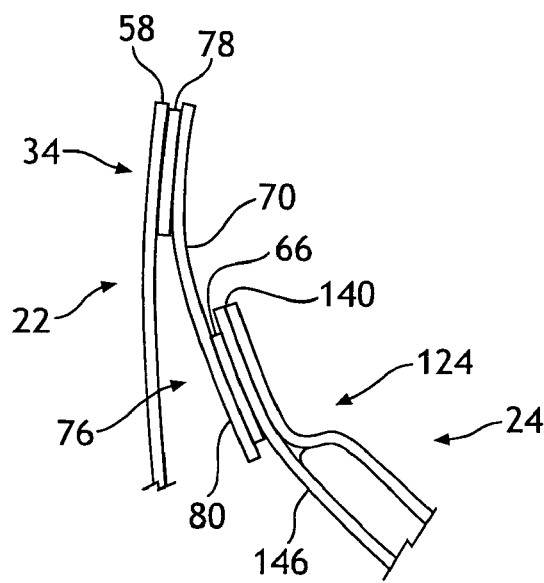
FIG. 10 is side cross-sectional view of a waist region of another embodiment of the absorbent garment of the present invention.
Figure 11:
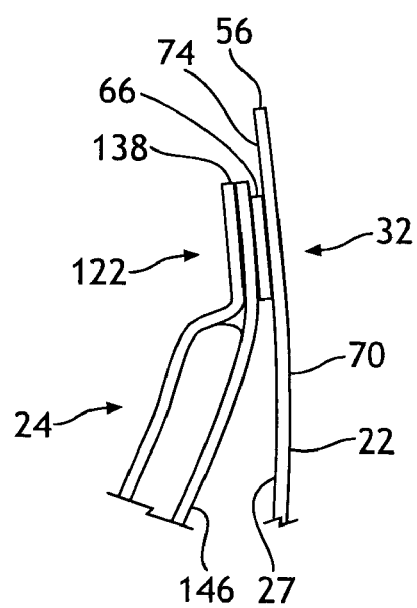
FIG. 11 is side cross-sectional view of a waist region of another embodiment of the absorbent garment of the present invention.

The garment shell 22 of the absorbent garment 10 of the present invention can, in various embodiments, include an inner attachment member 70 at either the front waist region 32 of the garment shell 22 or the back waist region 34 of the garment shell 22, or both. For example, the exemplary embodiments shown in FIGS. 2, 5-8 include a front inner attachment member 70 disposed at the front waist region 32 of the garment shell 22. FIG. 10 representatively illustrates a back inner attachment member 70 disposed at the back waist region 34 of the garment shell 22.

The inner attachment member 70 has a body-facing surface 72 and an opposite outward-facing surface 73. In particular embodiments, such as that illustrated in FIG. 6, the garment shell 22 is attached to the outward-facing surface 73 of the front inner attachment member 70, and the front fastening component 66 is attached to the body-facing surface 72 of the front inner attachment member 70. Alternatively, the configuration could be reversed (not shown), such that the garment shell 22 is attached to the body-facing surface 72 of the front inner attachment member 70, and the front fastening component 66 is attached to the outward-facing surface 73 of the front inner attachment member 70. In such an embodiment, the inner attachment member 70 may include a 180° fold at its longitudinal end nearest the front waist end 56 of the garment shell 22. In still another embodiment, both the garment shell 22 and the front fastening component 66 can be attached to the body-facing surface 72 of the inner attachment member 70. In such an embodiment, the inner attachment member 70 may include a 180° fold at its longitudinal end nearest the front waist end 56 of the garment shell 22. In yet another embodiment, both the garment shell 22 and the front fastening component 66 can be attached to the outward-facing surface 73 of the inner attachment member 70. In still another embodiment, the inner attachment member 70 can be embedded within the waist end 56, such as between the garment shell 22 and a waist elastic member 64.

In particular embodiments, the inner attachment member 70 is configured and sized such that the location at which the fastening component 66 on the absorbent assembly 24 is engaged to the inner attachment member 70 can be movably adjusted in the longitudinal direction. For example, in particular embodiments (FIGS. 1-2 and 5-8), the length dimension of the inner attachment member 70 is at least about twice the length dimension of the front fastening component 66, and more particularly at least about three times the length dimension of the front fastening component 66. Also, in particular embodiments (FIGS. 2, 8, and 9), the length dimension of the fastening component 68 on the garment shell 22 is at most about 40% greater than the length dimension of the back fastening component 66, and more particularly at most about 20% greater than the length dimension of the back fastening component 66. In one embodiment of the absorbent garment, the length dimension of the fastening component 68 on the garment shell 22 is roughly equal to the length dimension of the back fastening component 66.

In particular embodiments, the inner attachment member 70 is stretchable, and more suitably elastic. For example, the inner attachment member 70 can be stretchable to a length in the range of about 5 percent to about 75 percent of its unstretched length. The inner attachment member 70 is suitably constructed of elastomeric materials, including but not limited to elastic strands, elastic films, and nonwoven elastic webs such as meltblown or spunbond elastomeric fibrous webs. Examples of suitable elastomeric materials include ESTANE® elastomeric polyurethanes (available from B.F. Goodrich and Company located in Cleveland, Ohio), PEBAX® elastomers (available from AtoChem located in Philadelphia, Pa.), HYTREL® elastomeric polyester (available from E.I. DuPont de Nemours located in Wilmington Del.), KRATON® elastomer (available from Kraton Polymers, Inc. of Houston, Tex.), strands of LYCRA® elastomer (available from E.I. DuPont de Nemours located in Wilmington Del.) or the like, as well as combinations thereof. Suitable elastomeric materials may be braided, knit, woven or otherwise combined with natural fibers, or synthetic fibers such as polyester, nylon or polyolefins. Additional examples include stretch-bonded laminates and neck-bonded laminates. In desirable embodiments, the inner attachment member 70 comprises an elastomeric nonwoven material. Alternatively, the inner attachment member 70 can be constructed of an extensible material, or it may be constructed of a non-stretchable material, without departing from the scope of this invention.

The inner attachment member 70 suitably is in particular embodiments at least as wide as the absorbent assembly 24, such that the absorbent assembly 24 may be securely fastened to the inner attachment member 70 as previously described. In certain embodiments, the inner attachment member 70 is at least about as wide as the absorbent assembly 24, more particularly at least about 10% wider than the absorbent assembly 24, and still more particularly at least about 20% wider than the absorbent assembly 24. If the width of the inner attachment member 70 varies over its length, its width may be calculated as an average width. In other embodiments, the inner attachment member 70 is narrower than the absorbent assembly 24.

In still other embodiments, the inner attachment member 70 may include multiple layers. For example, the inner attachment member 70 can include a backing layer (not shown), such as nonwoven material or a polymeric film, and an attachment layer, such as a loop-type material as previously disclosed, secured to the backing layer. In such an embodiment, the attachment layer is adapted for refastenable engagement with the fasteners 66 on the absorbent assembly 24.

In those embodiments that include a front inner attachment member, the back waist end 140 of the absorbent assembly 24 can be attached to the back waist region 34 of the garment shell 22 in any number of ways. It can be permanently attached, as representatively illustrated in FIGS. 5 and 6. Alternatively, it can be removably attached, as representatively illustrated in FIG. 7. In that figure, the back waist region 124 of the absorbent assembly 24 includes a frangible line of weakness 90, such as perforations, to allow a user to disconnect at least a part of the absorbent assembly back waist region 124 from the absorbent garment 10. In yet another embodiment, as representatively illustrated in FIGS. 8 and 9, the back waist end 140 of the absorbent assembly 24 can be refastenably attached to the garment shell 22, such as by engagement of fastening components 66 and 68. In still another embodiment, as representatively illustrated in FIG. 10, the back waist region 124 of the garment shell 22 can include a back inner attachment member 70, to which the back waist region 124 of the absorbent assembly 24 can be refastenably attached. In such an embodiment, the back inner attachment member 70 can, in certain configurations, itself include a frangible line of weakness (not shown) to allow a user to completely disconnect the absorbent assembly back waist region 124 from the absorbent garment 10. Of course, a front inner attachment member can likewise include a frangible line of weakness in certain embodiments.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An absorbent garment, comprising:
    a garment shell defining a longitudinal axis, a transverse axis, a first waist edge generally parallel to the transverse axis, a first waist region contiguous with the first waist edge, a second waist edge generally parallel to the transverse axis, and a second waist region contiguous with the second waist edge;
    a first inner attachment member disposed at the first waist region, and a second inner attachment member disposed at the second waist region, each attachment member having a length dimension generally parallel to the longitudinal axis; and
    an absorbent assembly adapted for refastenable attachment to the garment shell, the absorbent assembly having an inner surface adapted for contact with a wearer's body, an outer surface opposite the inner surface, a first end region in facing relationship with the first waist region of the garment shell, and a second end region in facing relationship with the second waist region of the garment shell,
    wherein the absorbent assembly comprises a first fastening component disposed in the first end region, the first fastening component having a length dimension generally parallel to the longitudinal axis, and a second fastening component disposed in the second end region, the second fastening component having a length dimension generally parallel to the longitudinal axis, wherein the first fastening component is adapted for refastenable engagement to the first inner attachment member, and the second fastening component is adapted for refastenable engagement to the second inner attachment member,
    wherein the length dimension of the first inner attachment member is greater than the length dimension of the first fastening component and the second attachment member.

2. The absorbent garment as set forth in claim 1 wherein the absorbent garment has at least one outer leg opening and a pair of inner leg openings separate from and disposed within the garment shell, the absorbent assembly at least in part defining said inner leg openings of the absorbent garment, said garment shell defining said at least one outer leg opening of the absorbent garment.

3. The absorbent garment as set forth in claim 2 wherein the absorbent assembly is configured to provide an elastic fit of the absorbent assembly against the wearer's legs at the inner leg openings of the absorbent garment, the garment shell being configured to generally hang loose about the wearer's legs at the at least one outer leg opening of the absorbent garment.

4. The absorbent garment as set forth in claim 2 wherein the garment shell further defines a crotch region extending longitudinally between the first waist region and the second waist region of the garment shell, the crotch region of the garment shell at least in part defining a pair of outer leg openings of the absorbent garment which are separate from the inner leg openings of the absorbent garment,
    wherein the absorbent assembly further defines a crotch region extending longitudinally between and interconnecting the absorbent article first end region and an absorbent article second end region, wherein the crotch region of the absorbent assembly is free from attachment to the crotch region of the garment shell.

5. The absorbent garment as set forth in claim 1 wherein the absorbent garment defines a waist opening, at least one outer leg opening, and wherein the garment shell comprises a first panel assembly having laterally opposite side margins and a second panel assembly having corresponding laterally opposite side margins, the first panel assembly being in generally overlapping relationship with the second panel assembly at the side margins of said first and second panel assemblies, whereby the overlapped side margins define laterally opposite side seams of the absorbent garment extending from the waist opening to said at least one outer leg opening, the side margins being releasably attached to each other along at least a portion of at least a length of said side margins to define a refastenable portion of the side seams of the absorbent garment.

6. The absorbent garment as set forth in claim 1 wherein the first inner attachment member defines a variable location fastening surface.

7. The absorbent garment as set forth in claim 6 wherein the first fastening component is a hook material, and the first inner attachment member is at least in part constructed of a loop material adapted for refastenable engagement with said hook material.

8. The absorbent garment as set forth in claim 1 wherein the absorbent assembly comprises a liquid permeable liner defining the inner surface of the absorbent assembly, an outer cover defining the outer surface of the absorbent assembly, and an absorbent body disposed between the liner and the outer cover, wherein each of the fastening components are affixed to at least one of the liner and the outer cover.

9. The absorbent garment as set forth in claim 1, wherein the first inner attachment member is integrally formed with the garment shell.

10. The absorbent garment as set forth in claim 1, wherein the first inner attachment member is a separately provided element attached to the garment shell.

11. The absorbent garment as set forth in claim 10, wherein the first inner attachment member includes a longitudinal end flap portion directly unadhered to the garment shell, wherein the first fastening component is refastenably engaged to the end flap portion.

12. The absorbent garment as set forth in claim 11, wherein the end flap portion comprises at least about 50% of the length dimension of the first inner attachment member.

13. The absorbent garment as set forth in claim 11, wherein the end flap portion comprises at least about 75% of the length dimension of the first inner attachment member.

14. The absorbent garment as set forth in claim 11 wherein the first inner attachment member has a body-faceable surface and an opposite outward-faceable surface, the garment shell being attached to the outward-faceable surface of the first inner attachment member, the first fastening component being attached to the body-faceable surface of the first inner attachment member.

15. The absorbent garment as set forth in claim 1, wherein the first inner attachment member comprises a backing layer and a separately provided attachment layer secured to the backing layer.

16. The absorbent garment as set forth in claim 1, wherein the first inner attachment member comprises an elastomeric nonwoven material.

17. The absorbent garment as set forth in claim 1, wherein the first inner attachment member consists of an elastomeric nonwoven material.

18. The absorbent garment as set forth in claim 1, wherein the length dimension of the front inner attachment member is at least about twice the length dimension of the front fastening component.

19. The absorbent garment as set forth in claim 1, wherein the length dimension of the second inner attachment member is at most 30% greater than the length dimension of the second fastening component.

20. The absorbent garment as set forth in claim 1, wherein the length dimension of the second inner attachment member is equal to the length dimension of the second fastening component.

21. The absorbent garment as set forth in claim 1, wherein the first waist edge is the front waist edge, and the second waist edge is the back waist edge.

22. An absorbent garment, comprising:
a garment shell defining a longitudinal axis, a transverse axis, a front waist edge generally parallel to the transverse axis, a front waist region contiguous with the front waist edge, a back waist edge generally parallel to the transverse axis, and a back waist region contiguous with the back waist edge;
a front inner attachment member disposed at the front waist region, and a back inner attachment member disposed at the back waist region, each inner attachment member having a length dimension generally parallel to the longitudinal axis; and
an absorbent assembly disposed within the garment shell, the absorbent assembly having an inner surface adapted for contact with a wearer's body, an outer surface opposite the inner surface, a front end region in facing relationship with the front waist region of the garment shell, and a back end region in facing relationship with the back waist region of the garment shell,
wherein the absorbent assembly comprises a front fastening component at its front end region, the front fastening component having a length dimension generally parallel to the longitudinal axis, and a back fastening component at its back end region, the back fastening component having a length dimension generally parallel to the longitudinal axis, wherein the front fastening component is refastenably engaged to the front inner attachment member,
wherein the front inner attachment member and the front fastening component both define continuously variable fastening surfaces, and
wherein the length dimension of the front inner attachment member is greater than the length dimension of the the back inner attachment member.

23. A three-dimensional absorbent garment, comprising:
a garment shell defining a longitudinal axis, a transverse axis, a front waist edge generally parallel to the transverse axis, a front waist region contiguous with the front waist edge, a back waist edge generally parallel to the transverse axis, and a back waist region contiguous with the back waist edge, the front and back waist regions being connected to one another to define a waist opening and at least one leg opening;
a separately provided front inner attachment member attached to the garment shell front waist region, the front inner attachment member comprising an elastomeric, nonwoven material, and a back inner attachment member disposed at the back waist region, each attachment member having a length dimension generally parallel to the longitudinal axis, the front inner attachment member defining a longitudinal end flap portion directly unadhered to the garment shell for a distance of at least 75% of the length dimension of the front inner attachment member; and
an absorbent assembly disposed within the garment shell, the absorbent assembly having an inner surface adapted for contact with a wearer's body, an outer surface opposite the inner surface, a front end region in facing relationship with the front waist region of the garment shell, a back end region in facing relationship with the back waist region of the garment shell, and elasticized containment flaps, wherein the absorbent assembly comprises a separately provided front fastening component attached to its front end region, the front fastening component having a length dimension generally parallel to the longitudinal axis, and a separately provided back fastening component attached to its back waist region, the back fastening component having a length dimension generally parallel to the longitudinal axis, wherein the front fastening component is refastenably engaged directly to the front inner attachment member, and the back fastening component is refastenably engaged directly to the back inner attachment member, wherein the length dimension of the front inner attachment member is at least three times the length dimension of the front fastening component, such that a user may adjust a position of refastenable engagement along the length dimension of the front inner attachment member, and wherein the front inner attachment member is greater in length than the back inner attachment member.

24. The absorbent garment as set forth in claim 23, wherein the front and back inner attachment members comprise an elastomeric nonwoven material, and the front and back fastening components comprise a hook material refastenably engageable with the elastomeric nonwoven material.

\* \* \* \* \*